US011623956B2

United States Patent
Allan et al.

(10) Patent No.: US 11,623,956 B2
(45) Date of Patent: Apr. 11, 2023

(54) ANTI-HUMAN CD19 ANTIBODIES

(71) Applicant: Eli Lilly and Company, Indianapolis, IN (US)

(72) Inventors: Barrett Allan, Encinitas, CA (US); Jeffrey Streetman Boyles, Indianapolis, IN (US); Alison Lee Sim Budelsky, Solana Beach, CA (US); Kira Vladimirovna Rubtsova, San Diego, CA (US); Guifeng Zhang, San Diego, CA (US); Songqing Na, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 101 days.

(21) Appl. No.: 17/181,184

(22) Filed: Feb. 22, 2021

(65) Prior Publication Data

US 2021/0269520 A1 Sep. 2, 2021

Related U.S. Application Data

(60) Provisional application No. 62/983,093, filed on Feb. 28, 2020.

(51) Int. Cl.
| | | |
|---|---|---|
| *A61K 39/395* | (2006.01) |
| *A61K 39/00* | (2006.01) |
| *C12P 21/06* | (2006.01) |
| *C12P 5/02* | (2006.01) |
| *C12N 5/20* | (2006.01) |
| *C12N 15/00* | (2006.01) |
| *C07K 16/00* | (2006.01) |
| *C07K 16/46* | (2006.01) |
| *C07H 21/04* | (2006.01) |
| *C07K 16/28* | (2006.01) |
| *A61P 37/06* | (2006.01) |
| *A61P 19/02* | (2006.01) |

(52) U.S. Cl.
CPC .......... *C07K 16/2803* (2013.01); *A61P 19/02* (2018.01); *A61P 37/06* (2018.01); *A61K 2039/505* (2013.01); *C07K 2317/14* (2013.01); *C07K 2317/55* (2013.01); *C07K 2317/565* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

2018/0273621 A1 9/2018 Damschroder et al.

FOREIGN PATENT DOCUMENTS

WO 2007076950 A1 7/2007

OTHER PUBLICATIONS

Carter, et al., Immunol. Res. 26: 45-54, 2002.
Cree, et al., Lancet. 394(10206):1352-1363, 2019.
Kellner, et al., Leukemia. 27(7):1595-1598, 2013.
Kaplon, et al., MAbs. 12(1): 1703531, 2020.
Seidel, et al., Mol. Ther. 24(9):1634-43, 2016.
Szili, et al., MAbs. 6(4): 991-999, 2014.
Labrijn, et al., Nat. Biotechnol. 2009, 27(8):767.
Patent Cooperation Treaty International Search Report of the International Searching Authority pertaining to International Application No. PCT/US2021/018989; International filing date: Feb. 22, 2021; dated May 27, 2021.
Patent Cooperation Treaty Written Opinion of the International Searching Authority pertaining to International Application No. PCT/US2021/018989; dated Mar. 22, 2021.

*Primary Examiner* — Maher M Haddad
(74) *Attorney, Agent, or Firm* — Dipa Patel

(57) ABSTRACT

The present disclosure relates to antibodies that bind human CD19 ("anti-human CD19 antibodies" or "anti-human CD19 antibodies"), compositions comprising such anti-human CD19 antibodies, and methods of using such anti-human CD19 antibodies.

51 Claims, 17 Drawing Sheets

Specification includes a Sequence Listing.

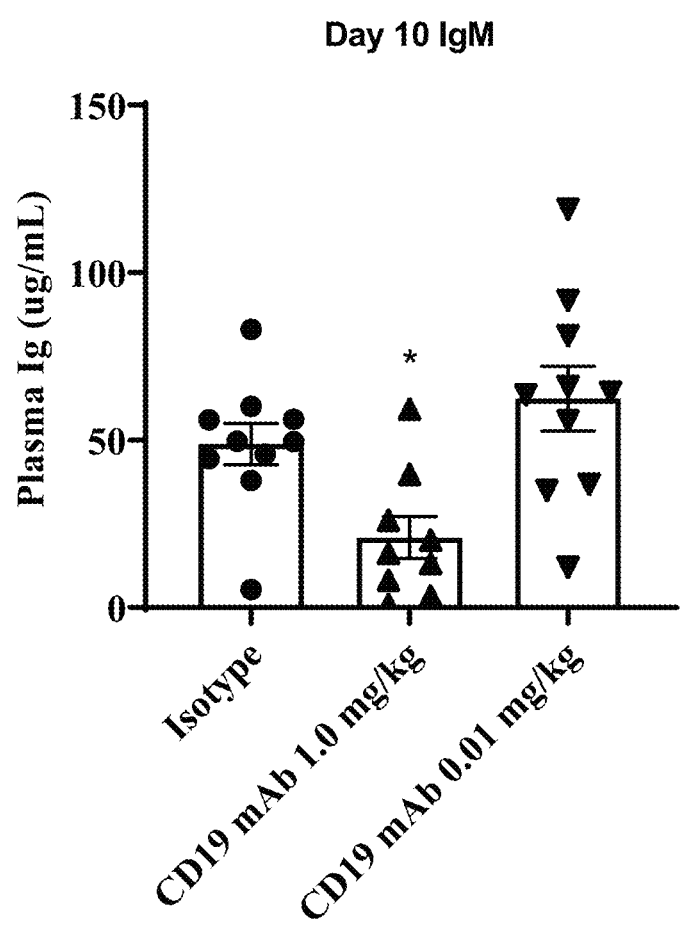

p < 0.05 (Statistical Method: One-way ANOVA on log-transformed data followed by Tukey's.
Bars with different letters were significantly different.)

ANTI-HUMAN CD19 ANTIBODIES

FIELD OF THE INVENTION

The present disclosure relates to antibodies that bind human CD19 ("anti-human CD19 antibodies" or "anti-CD19 antibodies"), compositions comprising such anti-human CD19 antibodies, and methods of using such anti-human CD19 antibodies.

BACKGROUND

B cells can produce antibodies against various antigens and thus play an important role in the humoral immune response. Additionally, B cells also function as antigen presenting cells (APC) and secrete cytokines. B cells express B cell receptor (BCR) on their cell membranes; and BCR allows the B cell to bind a specific antigen, against which it will initiate an antibody response. Dysregulation of B cells is associated with a variety of disorders.

Human B-lymphocyte antigen CD19 (also known as Cluster of Differentiation 19, B-lymphocyte surface antigen B4, T-Cell Surface Antigen Leu-12, or CVID3) is a transmembrane protein widely expressed during all phases of B cell development until its terminal differentiation into plasma cells. Thus, human CD19 is a pan-B cell marker. CD19 is found in association with CD21, a complement receptor, and with CD81, a member of the tetraspan family (Carter, et al., Immunol. Res. 26: 45-54, 2002). CD19 is a co-receptor for the BCR and acts as an adaptor protein to recruit cytoplasmic signaling proteins to the BCR complex. CD19 is required for normal B cell function and is involved in diverse B cell responses, including B cell survival, proliferation, activation, and differentiation.

Anti-human CD19 antibodies have been described previously and are being tested in clinical trials. Many known anti-human CD19 antibodies are B cell-depleting antibodies; for example, inebilizumab (also known as MEDI-551) and tafasitamab (also known as MOR208 or XmAb5574) in Phase III clinical trials, loncastuximab in Phase II clinical trial, 4G7SDIE and DI-B4 in Phase I clinical trial, were all reported to be B cell-depleting antibodies (Cree, et al., Lancet. 394(10206):1352-1363, 2019; Kellner, et al., Leukemia. 27(7):1595-1598, 2013; Kaplon, et al., MAbs. 12(1): 1703531, 2020; Seidel, et al., Mol. Ther. 24(9):1634-43, 2016; WO2007076950).

Obexelimab (also known as XmAb5871) is an Fc-engineered antibody that binds both CD19 and FcγRIIb, and inhibits B cell function by engaging the inhibitory FcγRIIb receptor signaling (Szili, et al., MAbs. 6(4): 991-999, 2014). However, high affinity binding of obexelimab to FcγRIIb could lead to non-specific binding to other cell types. In human patients, obexelimab was reported to have a short half-life, with $T_{1/2}$ of 3.5±1.0 days; and reduce peripheral human B cell counts, with a mean reduction of about 30-40% of the baseline level (Jaraczewska-Baumann, et al., European League Against Rheumatism (EULAR) 2015 Annual Meeting Poster: *A Phase 1b/2a Study of the Safety, Tolerability, Pharmacokinetics and Pharmacodynamics of XmAb®5871 in Patients with Rheumatoid Arthritis*, Jun. 12, 2015, available at https://investors.xencor.com/static-files/0017dcf1-deb2-46eb-93ff-90ba164ec50c).

Therefore, there remains a need for alternative anti-human CD19 antibodies that specifically bind and inhibit human B cells, without depleting them, for treating B cell associated disorders.

DETAILED DESCRIPTION

Provided herein are antibodies that bind human CD19 and inhibit B cell responses (e.g., proliferation, activation, and differentiation) without depleting the B cells (i.e., "non-depleting anti-human CD19 antibodies"). Such non-depleting anti-human CD19 antibodies can be used to treat B cell associated disorders, e.g., autoimmune diseases, without destroying those important immune cells, and thus avoid problematic concurrent immunocompromise, long-term immune suppression, and other complications resulting from B cell depletion. The anti-human CD19 antibodies provided herein have one or more of the following properties: 1) bind human CD19 (and sometimes cynomolgus monkey CD19) with desirable binding affinities and/or association and dissociation rates, 2) bind human B cells specifically and inhibit primary human B cell proliferation, activation and/or differentiation, 3) do not deplete human B cells, 4) being internalized into human B cells, 5) low immunogenicity risk, 6) low hydrophobicity, and/or 7) good stability, solubility, viscosity, and pharmacokinetic characteristics for development and use in the treatment of autoimmune disorders. As described below, in a side-by-side comparison, one such anti-human CD19 antibody CB3f is shown to bind human B cells with high specificity in a whole blood assay, whereas obexelimab shows non-specific binding to human neutrophils in addition to B cell binding. Since neutrophil is the most abundant type of white blood cells in human, the nonspecific binding to neutrophils might explain the short half-life of obexelimab observed in human patients. Additionally, in an in vitro B cell apoptosis assay, obeximab is shown to induce primary human B cell apoptosis in a dose-dependent manner, whereas the anti-human CD19 antibody CB3f does not induce apoptosis of primary human B cells in the same assay.

In one aspect, provided herein are novel non-depleting anti-human CD19 antibodies. In some embodiments, the anti-human CD19 antibodies are fully human antibodies.

In some embodiments, provided herein are antibodies that bind human CD19, wherein the antibodies comprise a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 29, the HCDR2 comprises SEQ ID NO: 30, the HCDR3 comprises SEQ ID NO: 31, the LCDR1 comprises SEQ ID NO: 32, the LCDR2 comprises SEQ ID NO: 33, and the LCDR3 comprises SEQ ID NO: 34. In some embodiments, the anti-human CD19 antibodies comprise a VH comprising SEQ ID NO: 37 and a VL comprising SEQ ID NO: 41.

In some embodiments, the anti-human CD19 antibody has a human IgG1 or IgG4 isotype. In some embodiments, the anti-human CD19 antibody has a human IgG4 isotype. In some embodiments, the anti-human CD19 antibody has a modified human IgG4 hinge region comprising a S228P mutation (according to the EU Index Numbering), which reduces the IgG4 Fab-arm exchange in vivo (see Labrijn, et al., Nat. Biotechnol. 2009, 27(8):767). In some embodiments, the anti-human CD19 antibody has a human IgG1 isotype. In some embodiments, the anti-human CD19 antibody has a modified human IgG1 Fc region that has reduced or eliminated Fc effector functions such as antibody-dependent cell cytotoxicity (ADCC) and complement-dependent cytotoxicity (CDC). Such an antibody is termed an "IgG1-effector null" antibody.

In some embodiments, the anti-human CD19 antibody has a human IgG4 isotype. For example, in some embodiments, the antibody comprises a heavy chain (HC) comprising SEQ ID NO: 35 and a light chain (LC) comprising SEQ ID NO: 39. In some embodiments, the antibody has a human IgG1 isotype. For example, in some embodiments, the antibody comprises a HC comprising SEQ ID NO: 50 and a LC comprising SEQ ID NO: 39. In some embodiments, the antibody is an IgG1-effector null antibody. For example, in some embodiments, the antibody comprises a HC comprising SEQ ID NO: 52 and a LC comprising SEQ ID NO: 39.

In some embodiments, provided herein are antibody fragments (e.g., Fab or scFv) that bind human CD19, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 29, the HCDR2 comprises SEQ ID NO: 30, the HCDR3 comprises SEQ ID NO: 31, the LCDR1 comprises SEQ ID NO: 32, the LCDR2 comprises SEQ ID NO: 33, and the LCDR3 comprises SEQ ID NO: 34. In some embodiments, the antibody fragments comprise a VH comprising SEQ ID NO: 37 and a VL comprising SEQ ID NO: 41.

Provided herein are also antibodies that bind human CD19, wherein the antibodies comprise a VH and a VL, wherein the VH comprises HCDR1, HCDR2, and HCDR3, and the VL comprises LCDR1, LCDR2, and LCDR3, wherein the HCDR1 comprises SEQ ID NO: 29, the HCDR2 comprises SEQ ID NO: 30, the HCDR3 comprises SEQ ID NO: 31, the LCDR1 comprises SEQ ID NO: 43, the LCDR2 comprises SEQ ID NO: 44, and the LCDR3 comprises SEQ ID NO: 45. In some embodiments, the anti-human CD19 antibodies comprise a VH comprising SEQ ID NO: 37 and a VL comprising SEQ ID NO: 48. In some embodiments, the antibody has a human IgG4 isotype. For example, in some embodiments, the antibody comprises a HC comprising SEQ ID NO: 35 and a LC comprising SEQ ID NO: 46. In some embodiments, the antibody has a human IgG1 isotype. For example, in some embodiments, the antibody comprises a HC comprising SEQ ID NO: 50 and a LC comprising SEQ ID NO: 46. In some embodiments, the antibody is an IgG1-effector null antibody. For example, in some embodiments, the antibody comprises a HC comprising SEQ ID NO: 52 and a LC comprising SEQ ID NO: 46.

In some embodiments, provided herein are antibody fragments (e.g., Fab or scFv) that bind human CD19, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 29, the HCDR2 comprises SEQ ID NO: 30, the HCDR3 comprises SEQ ID NO: 31, the LCDR1 comprises SEQ ID NO: 43, the LCDR2 comprises SEQ ID NO: 44, and the LCDR3 comprises SEQ ID NO: 45. In some embodiments, the antibody fragments comprise a VH comprising SEQ ID NO: 37 and a VL comprising SEQ ID NO: 48.

Also provided herein are antibodies that bind human CD19, wherein the antibodies comprise a VH and a VL, wherein the VH comprises HCDR1, HCDR2, and HCDR3, and the VL comprises LCDR1, LCDR2, and LCDR3, wherein the HCDR1 comprises SEQ ID NO: 15, the HCDR2 comprises SEQ ID NO: 16, the HCDR3 comprises SEQ ID NO: 17, the LCDR1 comprises SEQ ID NO: 18, the LCDR2 comprises SEQ ID NO: 19, and the LCDR3 comprises SEQ ID NO: 20. In some embodiments, the anti-human CD19 antibodies comprise a VH comprising SEQ ID NO: 23 and a VL comprising SEQ ID NO: 27. In some embodiments, the antibody has a human IgG4 isotype. For example, in some embodiments, the antibody comprises a HC comprising SEQ ID NO: 21 and a LC comprising SEQ ID NO: 25. In some embodiments, the antibody has a human IgG1 isotype. In some embodiments, the antibody is an IgG1-effector null antibody. For example, in some embodiments, the antibody comprises a HC comprising SEQ ID NO: 54 and a LC comprising SEQ ID NO: 25.

In some embodiments, provided herein are antibody fragments (e.g., Fab or scFv) that bind human CD19, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 15, the HCDR2 comprises SEQ ID NO: 16, the HCDR3 comprises SEQ ID NO: 17, the LCDR1 comprises SEQ ID NO: 18, the LCDR2 comprises SEQ ID NO: 19, and the LCDR3 comprises SEQ ID NO: 20. In some embodiments, the antibody fragments comprise a VH comprising SEQ ID NO: 23 and a VL comprising SEQ ID NO: 27.

Also provided herein are antibodies that bind human CD19, wherein the antibodies comprise a VH and a VL, wherein the VH comprises HCDR1, HCDR2, and HCDR3, and the VL comprises LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 4, the LCDR2 comprises SEQ ID NO: 5, and the LCDR3 comprises SEQ ID NO: 6. In some embodiments, the anti-human CD19 antibodies comprise a VH comprising SEQ ID NO: 9 and a VL comprising SEQ ID NO: 13. In some embodiments, the antibody comprises a HC comprising SEQ ID NO: 7 and a LC comprising SEQ ID NO: 11.

In some embodiments, provided herein are antibody fragments (e.g., Fab or scFv) that bind human CD19, wherein the antibody fragments comprise a VH and a VL, wherein the VH comprises HCDR1, HCDR2, and HCDR3, and the VL comprises LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 4, the LCDR2 comprises SEQ ID NO: 5, and the LCDR3 comprises SEQ ID NO: 6. In some embodiments, the antibody fragments comprise a VH comprising SEQ ID NO: 9 and a VL comprising SEQ ID NO: 13.

In another aspect, provided herein are nucleic acids encoding a heavy chain or light chain, or a VH or VL, of the novel anti-human CD19 antibodies described herein, and vectors comprising such nucleic acids.

In some embodiments, provided herein are nucleic acids encoding a heavy chain or light chain of the anti-human CD19 antibodies described herein. In some embodiments, provided herein are nucleic acids comprising a sequence encoding SEQ ID NO: 35, 52, 50, 39, 46, 21, 54, 25, 7 or 11. In some embodiments, provided herein are nucleic acids comprising a sequence encoding an antibody heavy chain that comprises SEQ ID NO: 35, 52, 50, 21, 54, or 7. For example, the nucleic acid can comprise a sequence selected from SEQ ID NO: 36, 53, 51, 22, 55, or 8. In some embodiments, provided herein are nucleic acids comprising a sequence encoding an antibody light chain that comprises SEQ ID NO: 39, 46, 25, or 11. For example, the nucleic acid can comprise a sequence selected from SEQ ID NO: 40, 47, 26, or 12.

Also provided herein are nucleic acids encoding a VH or VL of the anti-human CD19 antibodies described herein. In some embodiments, provided herein are nucleic acids comprising a sequence encoding SEQ ID NO: 37, 23, 27, 9, 41, 48, 13. In some embodiments, provided herein are nucleic acids comprising a sequence encoding an antibody VH that comprises SEQ ID NO: 37, 23, 27, 9. For example, the nucleic acid can comprise a sequence selected from SEQ ID NO: 38, 24, 28, 10. In some embodiments, provided herein are nucleic acids comprising a sequence encoding an antibody VL that comprises SEQ ID NO: 41, 48, 13. For example, the nucleic acid can comprise a sequence selected from SEQ ID NO: 42, 49, 14.

Provided herein are also vectors comprising a nucleic acid sequence encoding an antibody heavy chain or light chain. For example, such vectors can comprise a nucleic acid sequence encoding SEQ ID NO: 35, 52, 50, 39, 46, 21, 54, 25, 7, or 11. In some embodiments, the vector comprises SEQ ID NO: 36, 53, 51, 40, 47, 22, 55, 26, 8, or 12.

Provided herein are also vectors comprising a nucleic acid sequence encoding an antibody VH or VL. For example, such vectors can comprise a nucleic acid sequence encoding SEQ ID NO: 37, 23, 27, 9, 41, 48, or 13. In some embodiments, the vector comprises SEQ ID NO: 38, 24, 28, 10, 42, 49, or 14.

Provided herein are also vectors comprising a first nucleic acid sequence encoding an antibody heavy chain and a second nucleic acid sequence encoding an antibody light chain. In some embodiments, the vector comprises a first nucleic acid sequence encoding SEQ ID NO: 35, 50, or 52, and a second nucleic acid sequence encoding SEQ ID NO: 39 or 46. In some embodiments, the vector comprises a first nucleic acid sequence encoding SEQ ID NO: 21 or 54, and a second nucleic acid sequence encoding SEQ ID NO: 25.

In some embodiments, the vector comprises a first nucleic acid sequence encoding SEQ ID NO: 35 and a second nucleic acid sequence encoding SEQ ID NO: 39. In some embodiments, the vector comprises a first nucleic acid sequence encoding SEQ ID NO: 52 and a second nucleic acid sequence encoding SEQ ID NO: 39. In some embodiments, the vector comprises a first nucleic acid sequence encoding SEQ ID NO: 50 and a second nucleic acid sequence encoding SEQ ID NO: 39. In some embodiments, the vector comprises a first nucleic acid sequence encoding SEQ ID NO: 35 and a second nucleic acid sequence encoding SEQ ID NO: 46. In some embodiments, the vector comprises a first nucleic acid sequence encoding SEQ ID NO: 52 and a second nucleic acid sequence encoding SEQ ID NO: 46. In some embodiments, the vector comprises a first nucleic acid sequence encoding SEQ ID NO: 50 and a second nucleic acid sequence encoding SEQ ID NO: 46. In some embodiments, the vector comprises a first nucleic acid sequence encoding SEQ ID NO: 21 and a second nucleic acid sequence encoding SEQ ID NO: 25. In some embodiments, the vector comprises a first nucleic acid sequence encoding SEQ ID NO: 54 and a second nucleic acid sequence encoding SEQ ID NO: 25. In some embodiments, the vector comprises a first nucleic acid sequence encoding SEQ ID NO: 7 and a second nucleic acid sequence encoding SEQ ID NO: 11.

Also provided are compositions comprising a first vector comprising a nucleic acid sequence encoding an antibody heavy chain, and a second vector comprising a nucleic acid sequence encoding an antibody light chain. In some embodiments, the composition comprises a first vector comprising a nucleic acid sequence encoding SEQ ID NO: 35, 52, or 50, and a second vector comprising a nucleic acid sequence encoding SEQ ID NO: 39 or 46. In some embodiments, the composition comprises a first vector comprising a nucleic acid sequence encoding SEQ ID NO: 21 or 54, and a second vector comprising a nucleic acid sequence encoding SEQ ID NO: 25.

In some embodiments, the composition comprises a first vector comprising a nucleic acid sequence encoding SEQ ID NO: 35 and a second vector comprising a nucleic acid sequence encoding SEQ ID NO: 39. In some embodiments, the composition comprises a first vector comprising a nucleic acid sequence encoding SEQ ID NO: 52 and a second vector comprising a nucleic acid sequence encoding SEQ ID NO: 39. In some embodiments, the composition comprises a first vector comprising a nucleic acid sequence encoding SEQ ID NO: 50 and a second vector comprising a nucleic acid sequence encoding SEQ ID NO: 39. In some embodiments, the composition comprises a first vector comprising a nucleic acid sequence encoding SEQ ID NO: 35 and a second vector comprising a nucleic acid sequence encoding SEQ ID NO: 46. In some embodiments, the composition comprises a first vector comprising a nucleic acid sequence encoding SEQ ID NO: 52 and a second vector comprising a nucleic acid sequence encoding SEQ ID NO: 46. In some embodiments, the composition comprises a first vector comprising a nucleic acid sequence encoding SEQ ID NO: 50 and a second vector comprising a nucleic acid sequence encoding SEQ ID NO: 46. In some embodiments, the composition comprises a first vector comprising a nucleic acid sequence encoding SEQ ID NO: 21 and a second vector comprising a nucleic acid sequence encoding SEQ ID NO: 25. In some embodiments, the composition comprises a first vector comprising a nucleic acid sequence encoding SEQ ID NO: 54 and a second vector comprising a nucleic acid sequence encoding SEQ ID NO: 25. In some embodiments, the composition comprises a first vector comprising a nucleic acid sequence encoding SEQ ID NO: 7 and a second vector comprising a nucleic acid sequence encoding SEQ ID NO: 11.

Nucleic acids of the present disclosure may be expressed in a host cell, for example, after the nucleic acids have been operably linked to an expression control sequence. Expression control sequences capable of expression of nucleic acids to which they are operably linked are well known in the art. An expression vector may include a sequence that encodes one or more signal peptides that facilitate secretion of the polypeptide(s) from a host cell. Expression vectors containing a nucleic acid of interest (e.g., a nucleic acid encoding a heavy chain or light chain of an antibody) may be transferred into a host cell by well-known methods, e.g., stable or transient transfection, transformation, transduction or infection. Additionally, expression vectors may contain one or more selection markers, e.g., tetracycline, neomycin, and dihydrofolate reductase, to aide in detection of host cells transformed with the desired nucleic acid sequences.

In another aspect, provided herein are cells, e.g., host cells, comprising the nucleic acids, vectors, or nucleic acid compositions described herein. A host cell may be a cell stably or transiently transfected, transformed, transduced or infected with one or more expression vectors expressing all or a portion of an antibody described herein. In some embodiments, a host cell may be stably or transiently transfected, transduced or infected with an expression vector expressing HC and LC polypeptides of an antibody of the present disclosure. In some embodiments, a host cell may be stably or transiently transfected, transformed, transduced or infected with a first vector expressing HC polypeptides and a second vector expressing LC polypeptides of an antibody described herein. Such host cells, e.g., mammalian host cells, can express the anti-human CD19 antibodies described herein. Mammalian host cells known to be capable of expressing antibodies include CHO cells, HEK293 cells, COS cells, and NS0 cells.

In some embodiments, the cell, e.g., host cell, comprises a vector comprising a first nucleic acid sequence encoding SEQ ID NO: 35, 50, or 52, and a second nucleic acid sequence encoding SEQ ID NO: 39 or 46. In some embodiments, the cell, e.g., host cell, comprises a vector comprising a first nucleic acid sequence encoding SEQ ID NO: 21 or 54, and a second nucleic acid sequence encoding SEQ ID NO: 25.

In some embodiments, the cell, e.g., host cell, comprises a first vector comprising a nucleic acid sequence encoding SEQ ID NO: 35, 52, or 50, and a second vector comprising a nucleic acid sequence encoding SEQ ID NO: 39 or 46. In some embodiments, the cell, e.g., host cell, comprises a first vector comprising a nucleic acid sequence encoding SEQ ID NO: 21 or 54, and a second vector comprising a nucleic acid sequence encoding SEQ ID NO: 25.

The present disclosure further provides a process for producing an anti-human CD19 antibody described herein by culturing the host cell described above, e.g., a mammalian host cell, under conditions such that the antibody is expressed and recovering the expressed antibody from the culture medium. The culture medium, into which an antibody has been secreted, may be purified by conventional techniques. Various methods of protein purification may be employed, and such methods are known in the art and described, for example, in Deutscher, Methods in Enzymology 182: 83-89 (1990) and Scopes, Protein Purification: Principles and Practice, 3rd Edition, Springer, NY (1994).

Also provided are antibodies produced by any of the processes described herein.

In another aspect, provided herein are pharmaceutical compositions comprising an antibody, nucleic acid, or vector described herein. Such pharmaceutical compositions can also comprise one or more pharmaceutically acceptable excipient, diluent or carrier. Pharmaceutical compositions can be prepared by methods well known in the art (e.g., *Remington: The Science and Practice of Pharmacy*, 22nd ed. (2012), A. Loyd et al., Pharmaceutical Press).

The anti-human CD19 antibodies, nucleic acids, vectors, or pharmaceutical compositions described herein can be used for treating B cell associated disorders. Because of their critical role in regulating the immune system, dysregulation of B cells is associated with a variety of disorders. B cell associated disorders include autoimmune diseases, which are caused by activation of self-reactive B cells and T cells, and lymphomas and leukemias, which are caused by excessive and/or uncontrolled B cell proliferation. Examples of B cell associated autoimmune diseases include rheumatoid arthritis, systemic lupus erythematosus, multiple sclerosis, Sjogren's syndrome, idiopathic thrombocytopenia purpura, Type 1 diabetes, Pemphigus vulgaris, Neuromyelitis optica, ANCA vasculitis (anti-neutrophil cytoplasmic antibody-associated vasculitis), Myasthenia gravis.

Given the anti-human CD19 antibodies described herein do not deplete B cells, they offer advantages over the B cell depleting antibodies for treating autoimmune diseases and can avoid problematic concurrent immunocompromise, long-term immune suppression, and other complications resulting from B cell depletion. As shown below, the anti-human CD19 antibodies described herein are internalized in primary human B cells. Thus, the anti-human CD19 antibodies described herein can also be used to deliver other therapeutic agents into human B cells.

In some embodiments, provided herein are methods of treating a B cell associated disorder, e.g., an autoimmune disease, in a subject (e.g., a human patient) in need thereof, by administering to the subject a therapeutically effective amount of an anti-human CD19 antibody, a nucleic acid encoding such an anti-human CD19 antibody, a vector comprising such a nucleic acid, or a pharmaceutical composition comprising such an anti-human CD19 antibody, nucleic acid or vector, as described herein. The antibodies, nucleic acids, vectors, or pharmaceutical compositions described herein may be administered by parenteral routes (e.g., subcutaneous and intravenous). In some embodiments, the B cell associated disorder is selected from systemic lupus erythematosus, multiple sclerosis, rheumatoid arthritis, Sjogren's syndrome, idiopathic thrombocytopenia purpura, Type 1 diabetes, Pemphigus vulgaris, Neuromyelitis optica, ANCA vasculitis, Myasthenia gravis.

Also provided are anti-human CD19 antibodies, nucleic acids, vectors, or pharmaceutical compositions described herein for use in therapy. Furthermore, the present disclosure also provides anti-human CD19 antibodies, nucleic acids, vectors, or pharmaceutical compositions described herein for use in the treatment of a B cell associated disorder, e.g., e.g., an autoimmune disease, e.g., systemic lupus erythematosus, multiple sclerosis, rheumatoid arthritis, Sjogren's syndrome, idiopathic thrombocytopenia purpura, Type 1 diabetes, Pemphigus vulgaris, Neuromyelitis optica, ANCA vasculitis, Myasthenia gravis.

Provided herein are also use of the anti-human CD19 antibodies, nucleic acids, vectors, or pharmaceutical compositions described herein in the manufacture of a medicament for the treatment of a B cell associated disorder, e.g., an autoimmune disease, e.g., systemic lupus erythematosus, multiple sclerosis, rheumatoid arthritis, Sjogren's syndrome, idiopathic thrombocytopenia purpura, or Type 1 diabetes, Pemphigus vulgaris, Neuromyelitis optica, ANCA vasculitis, Myasthenia gravis.

As used herein, the term "a," "an," "the" and similar terms used in the context of the present disclosure (especially in the context of the claims) are to be construed to cover both the singular and plural unless otherwise indicated herein or clearly contradicted by the context.

The term "antibody," as used herein, refers to an immunoglobulin molecule that binds an antigen. Embodiments of an antibody include a monoclonal antibody, polyclonal antibody, human antibody, humanized antibody, chimeric antibody, or conjugated antibody. The antibodies can be of any class (e.g., IgG, IgE, IgM, IgD, IgA) and any subclass (e.g., IgG1, IgG2, IgG3, IgG4).

An exemplary antibody is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212). The North CDR definitions are used for the anti-human CD19 antibodies described herein.

Exemplary embodiments of antibodies of the present disclosure also include antibody fragments or antigen-binding fragments, which comprise at least a portion of an antibody retaining the ability to specifically interact with an antigen such as Fab, Fab', F(ab')2, Fv fragments, scFv, scFab, disulfide-linked Fvs (sdFv), a Fd fragment and linear antibodies.

The terms "bind" and "binds" as used herein are intended to mean, unless indicated otherwise, the ability of a protein or molecule to form a chemical bond or attractive interaction with another protein or molecule, which results in proximity of the two proteins or molecules as determined by common methods known in the art.

The term "CD19" as used herein, unless stated otherwise, refers to human B-lymphocyte antigen CD19 (also known as Cluster of Differentiation 19, B-lymphocyte surface antigen B4, T-Cell Surface Antigen Leu-12, or CVID3). The amino acid sequence of human CD19 is known in the art, e.g., NCBI Reference Sequence NP_001171569.1 (isoform 1, SEQ ID NO: 56) or NP_001761.3 (isoform 2, SEQ ID NO: 57). Isoform 2 is a splice variant of isoform 1 and is one amino acid shorter than isoform 1 in the intracellular domain. The term "CD19" is used herein to refer collectively to all known human CD19 isoforms and polymorphic forms.

The term "Fc region" as used herein refers to a region of an antibody, which comprises the CH2 and CH3 domains of the antibody heavy chain. Optionally, the Fc region may include a portion of the hinge region or the entire hinge region of the antibody heavy chain.

The term "non-depleting antibody" as used herein refers to an antibody that does not significantly reduce B cell numbers in a subject after treatment, as compared to the B cell numbers before the treatment. B cell number can be measured using well-known assays such as those described in the Examples. A non-depleting antibody typically does not induce antibody dependent cellular cytotoxicity (ADCC), antibody dependent cellular phagocytosis (ADCP), complement dependent cellular cytotoxicity (CDC), or apoptosis of the B cells.

The terms "nucleic acid" or "polynucleotide", as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction.

The term "subject", as used herein, refers to a mammal, including, but are not limited to, a human, chimpanzee, ape, monkey, cattle, horse, sheep, goat, swine, rabbit, dog, cat, rat, mouse, guinea pig, and the like. Preferably the subject is a human.

The term "therapeutically effective amount," as used herein, refers to an amount of a protein or nucleic acid or vector or composition that will elicit the biological or medical response of a subject, for example, reduction or inhibition of an enzyme or a protein activity, or ameliorate symptoms, alleviate conditions, slow or delay disease progression, or prevent a disease, etc. In a non-limiting embodiment, the term "a therapeutically effective amount" refers to the amount of a protein or nucleic acid or vector or composition that, when administered to a subject, is effective to at least partially alleviate, inhibit, prevent and/or ameliorate a condition, or a disorder or a disease.

As used herein, "treatment" or "treating" refers to all processes wherein there may be a slowing, controlling, delaying or stopping of the progression of the disorders or disease disclosed herein, or ameliorating disorder or disease symptoms, but does not necessarily indicate a total elimination of all disorder or disease symptoms. Treatment includes administration of a protein or nucleic acid or vector or composition for treatment of a disease or condition in a patient, particularly in a human.

BRIEF DESCRIPTION OF THE DRAWINGS

FIGS. 9A-9B show the reduction of human IgM in NSG mice treated with anti-human CD19 mAb CB3f on Day 6 (FIG. 9A) and Day 10 (FIG. 9B) after treatment.

FIG. 13A shows treatment with the non-depleting CD19 surrogate Ab in semi-established mode reduced clinical score greater than the depleting CD20 surrogate Ab in the mouse CIA model. Clinical scores of mice between Day 21 and Day 42 of the study (n=12/group except n=5 for Isotype control treated no disease control group). Symbols represent mean of group and error bars represent standard error of the mean (SEM). Animals were dosed starting Day 19. FIG. 13B shows treatment with the non-depleting CD19 surrogate Ab reduced clinical score AUC (Days 24 to 42) greater than the depleting CD20 surrogate Ab in the mouse CIA model. Clinical score AUCs of mice between Day 24 and Day 42 of the study (n=12/group except n=5 for isotype control treated no disease control group). Bars represent mean of group and error bars represent standard error of the mean (SEM). Mice were dosed starting Day 19. Bars that do not share a common letter are significantly different from each other ($p<0.05$ one-way analysis of variance (ANOVA) Tukey's post-hoc).

EXAMPLES

The following examples are offered to illustrate, but not to limit, the claimed invention.

Example 1. Generation of Antibodies that Bind Human CD19 (Anti-Human CD19 Antibodies)

Anti-human CD19 antibody C323 is discovered from a phage display library using cell-based panning against human embryonic kidney (HEK) cells co-transfected with human CD19 (SEQ ID NO: 56) and its co-receptor CD21. A negative panning against parental HEK-293 cells is used to remove non-specific cell binders. CD19-specific binding is confirmed using CD19 extracellular domain (ECD) protein by ELISA. Following conversion to IgG format and purification, cell binding is confirmed using Daudi human Burkitt's lymphoma cell line and isolated primary human B cells by FACS.

Figure 1A:
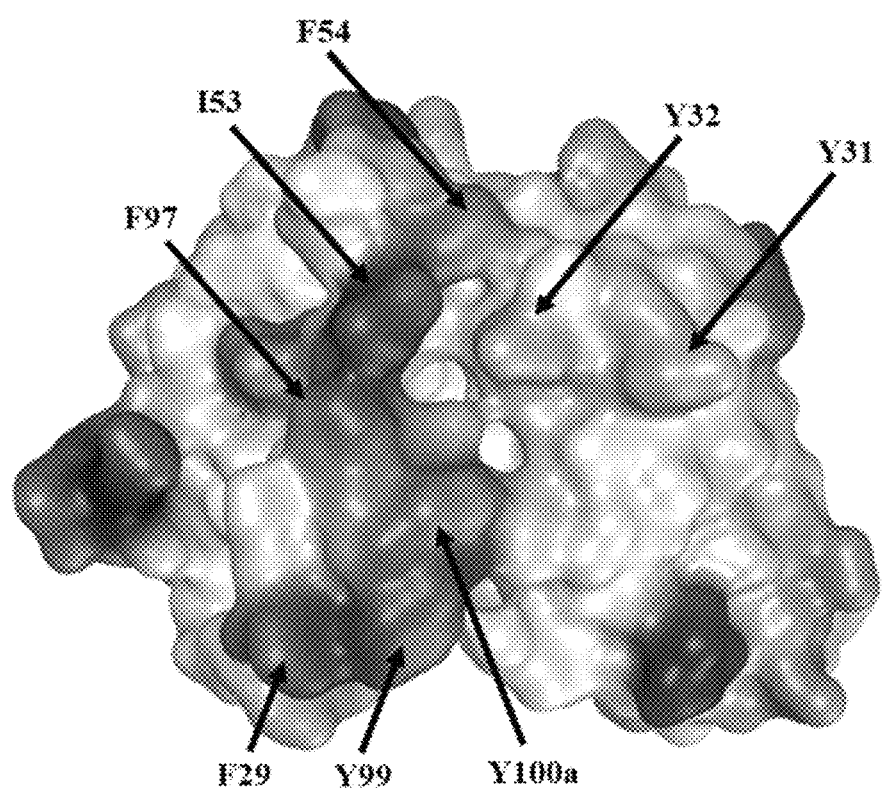
FIGS. 1A-1B show the surface hydrophobicity profiles of the anti-human CD19 parental antibody C323 (FIG. 1A) and the optimized anti-human CD19 antibody CB3f (FIG. 1B).

Hydrophobic interaction chromatography (HIC) is a technique for separation of proteins commonly used for characterization of antibody variants; and the retention time to the HIC column of a protein of interest reflects its overall hydrophobicity (J Pharm Biomed Anal. 2016 130:3-18). C323 is deemed to be hydrophobic due to prolonged HIC column retention time. Antibody hydrophobicity can cause manufacture problems such as poor expression and protein aggregation. Targeted and random mutagenesis is used to enhance the biophysical properties of C323 and increase its affinity and potency. A homology model of the variable region of the C323 anti-human CD19 parental mAb is created. A spatial aggregation propensity algorithm is then applied to the model to identify surface exposed hydrophobic patches. This process identifies eight surface-exposed hydrophobic residues within LCDR1, HCDR2 and HCDR3: LCDR1:Y31, Y32; HCDR2:I52, I53 and F54; HCDR3: F97, Y99 and Y100a (Kabat numbering) (FIG. 1A). These residues are targeted for mutagenesis. Libraries are created to include more hydrophilic (polar or charged) amino acids using VVK codon-based mutagenic oligonucleotides and incorporated using Kunkel mutagenesis into an uracil-containing single-stranded DNA template encoding the original C323 parental antibody with the selected CDR sequences deleted. Phage-expressed Fabs are screened using biotinylated human CD19 ECD antigen. Affinity neutral mutations identified in this manner are DNA sequenced and unique clones expressed as periplasmic Fab in *E. coli* and analyzed by titration ELISA. This process identified three affinity neutral but more hydrophilic amino acid substitutions: LCDR1:Y31H, HCDR2:F54Y and HCDR3:Y99K (Kabat numbering).

In parallel, optimization to increase affinity is done using NNK codon-based mutagenic oligonucleotides targeting all six CDRs and incorporated using Kunkel mutagenesis into an uracil-containing single-stranded DNA template with the selected CDRs deleted. Screening of phage-expressed Fab variants is done by capture-lift (Anal Biochem. 1998 256 (2):169-77) and ELISA using a biotinylated human CD19 ECD antigen. In this manner, CDR substitutions leading to increased affinity are identified: HCDR1:F29I, I34Y; HCDR2:G55D, HCDR3:G100bA; LCDR1:G27aK, A34H, LCDR2:S52R, A55P, LCDR3:N93Q (Kabat numbering) and combined, leading to the generation of C323.C1.

The three hydrophilic substitutions described above (Y31H, F54Y and Y99K) are added to C323.C1, generating a Fab template that is used for a final round of CDR randomization using NNK codon-based mutagenesis. Beneficial CDR mutations are combined in a library allowing all the beneficial mutations to be randomly combined or back-mutated to wild type sequence. This process identifies a high-affinity variant termed CB3. CB3 contains additional CDR residue substitutions: HCDR1:G27H, HCDR2:G50D, I53A, D55G, T56S, A57P; LCDR1:K27aH, H34A, LCDR3: L95Q (Kabat numbering).

Using CB3 as a template, additional CDR changes are made to revert specific residues to human IGKV3-20 germline identity. One residue in LCDR1:N29S and five residues in LCDR2:A50G, T51A, R52S, T53S, P55A are simultaneously reverted with minimal impact on the antibody's functions. This resulted in a final molecule called CB3f.

Several versions of the CB3f are generated, including (1) an IgG4 isotype comprising a HC of SEQ ID NO: 35 and a LC of SEQ ID NO: 39; (2) an IgG1 isotype comprising a HC of SEQ ID NO: 50 and a LC of SEQ ID NO: 39, and (3) an IgG1 effector null antibody comprising a HC of SEQ ID NO: 52 and a LC of SEQ ID NO: 39. Unless otherwise specified, "CB3f" refers to the IgG4 isotype comprising a HC of SEQ ID NO: 35 and a LC of SEQ ID NO: 39.

Figure 1B:
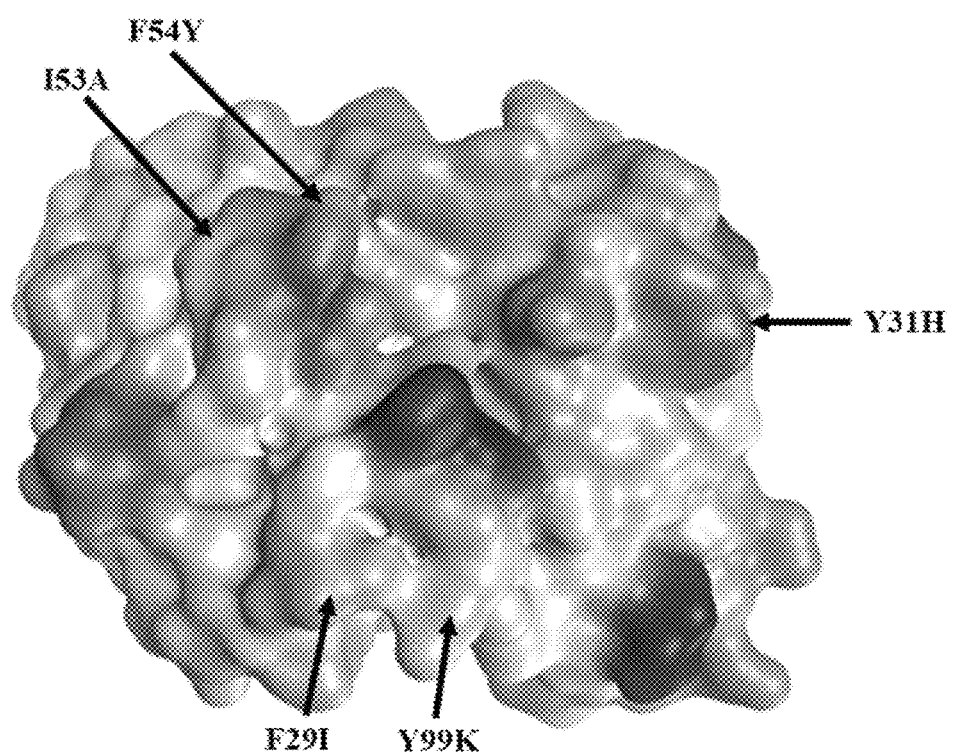

FIGS. 1A-1B show the improved surface hydrophobicity profile of CB3f compared to the parental antibody C323. The retention time of CB3f on a HIC column was reduced more than two folds when compared to the parental antibody C323. At the same time, the CB3f antibody titer from a transient CHO expression has increased more than two fold when compared to the parental C323 antibody titer.

Figure 2:
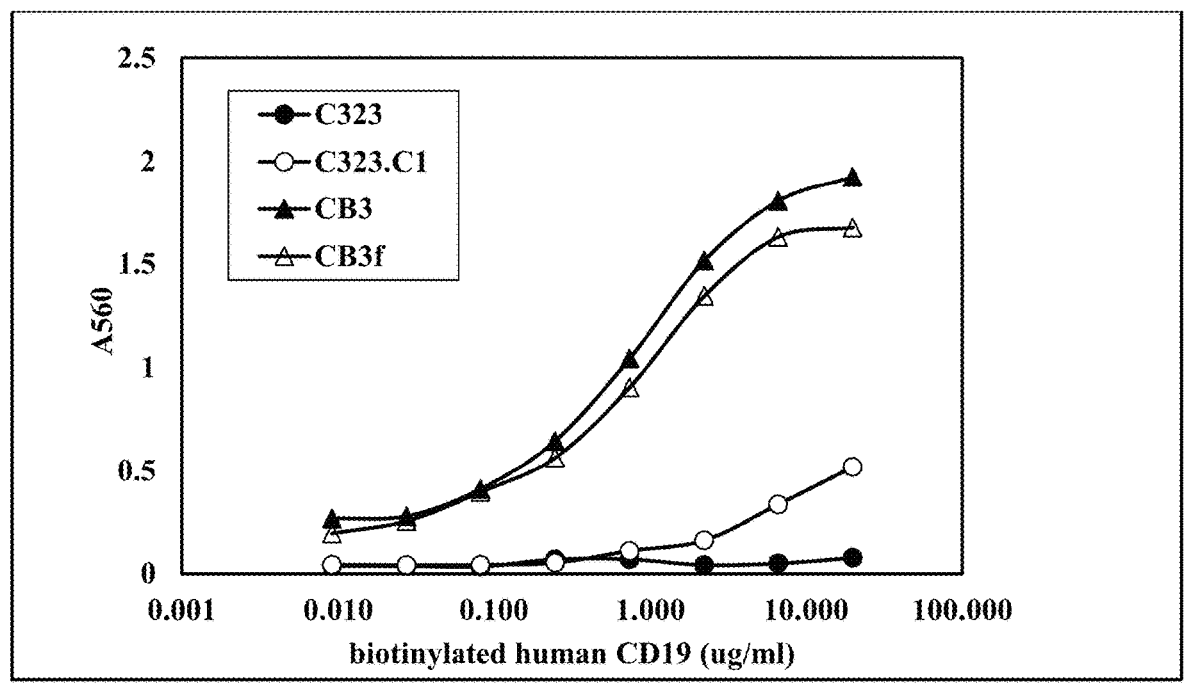
FIG. 2 shows the binding of anti-human CD19 antibodies to human CD19 in an ELISA assay.

FIG. 2 shows the improved binding to human CD19 by the affinity engineered antibodies CB3 and CB3f, when compared to C323 and C323.C1, in an ELISA assay. The ELISA assay is performed as follows. A 96 well microtiter plate is coated overnight at 4° C. using 50 μL/well of goat anti-human kappa polyclonal antibody diluted to 5 μg/mL in phosphate buffered saline (PBS). Following overnight incubation, the plate is aspirated and blocked using 200 μL of casein buffer for 1 hour at room temperature. The plate is washed three times using PBST (PBS with 0.1% Tween). The anti-human CD19 antibodies are diluted to 5 μg/mL in PBS casein and 50 μL added to each column of the anti-human kappa coated casein blocked plate for 1 hour at 37° C. The plate is washed three times using PBST. Biotinylated human CD19 extracellular domain protein is serially diluted from 20 μg/mL to 9 ng/mL and 50 μL added to the plates and incubated for 1 hour at 37° C. The plate is washed three times using PBST and then transferred to a beaker containing 1 liter of PBST and incubated with stirring overnight (approx. 16 hr) at 37° C. The wash buffer is aspirated and 50 μL of neutravidin alkaline phosphatase-conjugate diluted 1:1000 in casein buffer is added and incubated for 1 hour at 37° C. The plate is washed three times using PBS 0.1% Tween. Fifty μL of AMP-PMP substrate diluted 1:35 in deionized water is added and the absorbance at 560 nm read on a Spectramax plate reader.

As shown below, CB3f shows high affinity binding to human CD19 expressing CHO cells and has unexpectedly acquired binding to cynomolgus monkey CD19 expressing CHO cells. CB3f has 92% and 96% identity to human IGHV1-69 and IGKV3-20 germlines, respectively. Hence the anti-human CD19 antibody CB3f has high affinity, low hydrophobicity and high percentage of human germline identity, i.e., low immunogenicity risk.

The anti-human CD19 antibodies described herein, including but not limited to, CB3f, can be expressed in a mammalian cell line such as HEK293 or CHO, either transiently or stably transfected with an expression system for secreting the antibody using an optimal predetermined HC:LC vector ratio or a single vector system encoding both HCs and LC. Clarified media, into which the antibody has been secreted, can be purified using the commonly used techniques. The purity of the antibody, after these chromatography steps, may achieve a value greater than 99.0% (monomer).

Example 2. Characterization of the Anti-Human CD19 Antibodies

Binding Affinity to CD19

The solution-phase equilibrium binding affinities of the anti-human CD19 mAb CB3f to membrane-bound human CD19 and cynomolgus monkey CD19 stably expressed on CHO cells are measured by an MSD solution equilibrium titration (MSD-SET) assay at 37° C. Additionally, the monovalent affinity and kinetics of CB3f Fab fragment binding to CD19 are measured by surface plasmon resonance (SPR) at 37° C.

An MSD SI6000 instrument (Meso Scale Discovery, Rockville, Md.) is used for reading MSD plates. MSD assay plates are prepared as follows. A multi-array 96-well plate (Meso Scale Discovery, P/N L15XA-3) is coated overnight at 4° C. with a 1 μg/mL solution of a goat anti-human Fc capture antibody (Jackson ImmunoResearch, P/N 109-005-098) in PBS. Plates are washed 3× in TBS+0.1% Tween-20 (TBST) following coating.

CHO cells stably expressing human and cynomolgus monkey CD19 cells are fixed in 1% paraformaldehyde in PBS for 5 minutes at room temperature. Paraformaldehyde is removed by washing with PBS, and the cells are stored at 4° C. in 1% Blocker A (diluted from 3% Blocker A, Meso Scale Discovery, P/N R93AA-1) with 0.05% (w/v) sodium azide.

For the human CD19 affinity measurement, samples are prepared in duplicates with a fixed antibody concentration of 400 pM, 80 pM, 16 pM and 3.2 pM. For the cynomolgus monkey CD19 affinity measurement, samples are prepared in duplicates with a fixed antibody concentration of 10 nM, 2 nM, 400 pM, and 80 pM. Fixed human CD19 CHO cells are pelleted by centrifugation and resuspended in 3% Blocker A solution at $22 \times 10^6$ cells/mL. Fixed cynomolgus monkey CD19 CHO cells are pelleted by centrifugation and resuspended in 3% Blocker A solution at $200 \times 10^6$ cells/mL. The cells are serially diluted 2.5-fold in a conical-bottom 96-well plate in 3% Blocker A down to approximately 900 cells/mL for human CD19 and 8,400 cell/mL for cynomolgus monkey CD19 for a total of 12 cell dilutions each. These are mixed 1:1 with previously prepared antibody dilutions. For human CD19, the final antibody concentrations are 200 pM, 40 pM, 8 pM and 1.6 pM, and the final cell dilutions of $11 \times 10^6$ cells/mL down to approximately 450 cells/mL. For cynomolgus monkey CD19, the final antibody concentrations are 5 nM, 1 nM, 200 pM and 40 pM, and the final cell dilutions of $100 \times 10^6$ cells/mL down to approximately 4,200 cells/mL. The plate is incubated on a plate shaker at 37° C. for 3-4 days for human CD19 and 2 days for cynomolgus monkey CD19 to allow binding to reach equilibrium.

Following incubation, cells are pelleted by centrifugation. One hundred microliters of the clarified supernatant from the plate is transferred to the prepared MSD plate and incubated on a plate shaker at room temperature for 60 minutes. Following incubation, the plate is washed 3× with TBST, then 100 μL of 1 μg/mL biotinylated goat anti-human IgG primary antibody (Southern Biotech, Catalog 2010-08) in 1% Blocker A is added to all wells. This is incubated on a plate shaker at room temperature for 60 minutes. The plate was washed 3× with TBST, then 100 μL of 1 μg/mL SULFO-TAG streptavidin (Meso Scale Discovery, P/N R32AD-1) in 1% Blocker A was added to all wells. This was incubated on a plate shaker at room temperature for 60 minutes. The plate is washed 3× with TBST, then 1× Read Buffer T (Meso Scale Discovery, P/NR92TC-1) is added immediately before reading the plate. Dissociation constant ($K_D$) and a least common multiplier (LCM) to account for unknown antigen concentrations on cells are globally fit from the MSD-SET data to an equilibrium binding equation (see Darling and Brault, 2005, Kinetic Exclusion Assay Technology: Characterization of Molecular Interactions. Assay and Drug Development Technologies 2: 647-657) using non-linear regression in GraphPad Prism.

Biacore T200 instrument (GE Healthcare Life Sciences), reagents, and Biacore T200 Evaluation Software Ver 3.1 are used for the surface plasmon resonance analysis of human, mouse and cynomolgus monkey CD19 binding to the Fab fragment of CB3f. Recombinant CD19-Fc proteins are purchased from R&D Systems. A protein A sensor chip (GE protein A chip P/N 2912755) is used. Running buffer is 1×HBS-EP+ (Teknova P/N H8022), and running temperature is 37° C.

CD19 Fc fusion proteins are diluted to 3 μg/mL in running buffer, and approximately 60 RU each of human, cynomolgus monkey, and mouse proteins are captured in flow cells (Fc) 2, 3 and 4, respectively. CB3f Fab fragment is diluted to 1000 nM in running buffer and then 5-fold serially diluted in running buffer to 1.6 nM for a total of 5 dilutions. Fab or buffer blank is injected at 50 µL/min for 300 seconds followed by a 900 second dissociation phase. Regeneration is performed by injecting 10 mM glycine pH 1.5 for 30 seconds at 50 µL/min over all Fc. Reference-subtracted data is collected as Fc2-Fc1, Fc3-Fc1 and Fc4-Fc1, and then reference-subtracted data is blank subtracted. The on-rate ($k_{on}$) and off-rate ($k_{off}$) are fit using the "1:1 Binding" model. The affinity ($K_D$) is calculated from the binding kinetics according to the relationship: $K_D=k_{off}/k_{on}$.

CB3f binds to human and cynomolgus monkey CD19 expressed on CHO cells with an affinity ($K_D$) of 3.35 pM and 45.2 pM, respectively (Table 1).

The Fab fragment of CB3f binds to human CD19 with an on-rate ($k_{on}$) of $3.20 \times 10^6$ M$^{-1}$s$^{-1}$, an off-rate ($k_{off}$) of $2.35 \times 10^{-4}$ s$^{-1}$, and an affinity ($K_D$) of 76.8 pM (Table 2). The Fab fragment of CB3f binds to cynomolgus monkey CD19 with an on-rate ($k_{on}$) of $1.04 \times 10^6$ M$^{-1}$s$^{-1}$, an off-rate ($k_{off}$) of $9.78 \times 10^{-2}$ s$^{-1}$, and an affinity ($K_D$) of 94.5 nM (Table 2). No binding to mouse CD19 is observed at 1 µM Fab concentration.

TABLE 1

In vitro binding of CB3f to fixed CHO cells expressing either human or cynomolgus monkey CD19.
[Measured by MSD-SET at 37° C. Results are reported as the geometric mean of the $K_D$ from 3 independent replicates. Error estimate is calculated as geometric mean × standard deviation $\log_{10} K_D \times \ln 10$]

| Species | mAb Affinity (pM) |
|---|---|
| Human CD19 | 3.35 ± 0.56 |
| Cynomolgus monkey CD19 | 45.2 ± 2.8 |

TABLE 2

In vitro binding parameters of the Fab fragment of CB3f to human, cynomolgus monkey, and mouse CD19 Fc fusion proteins.
[Measured by Surface Plasmon Resonance (SPR) at 37° C. Results are reported as the mean ± standard deviation of 3 independent replicates.]

| Species | Fab On-Rate ($k_{on}$) (M$^{-1}$s$^{-1}$ × $10^6$) | Fab Off-Rate ($k_{off}$) (s$^{-1}$ × $10^{-4}$) | Fab Affinity ($K_D$) (pM) |
|---|---|---|---|
| Human CD19 | 3.20 ± 1.15 | 2.35 ± 0.37 | 76.8 ± 16.0 |
| Cynomolgus monkey CD19 | 1.04 ± 0.03 | 978 ± 79 | 94,500 ± 7,900 |
| Mouse CD19 | No binding observed at 1 µM Fab concentration | | |

Stability

Stability of CB3f is assessed at a high concentration (approximately 100 mg/mL) in 5 mM histidine buffer (pH 6.0) with excipients. Concentrated samples are incubated for a period of 4 weeks at 5° C. and 35° C. Following incubation, samples are analyzed for the percentage of high molecular weight (% HMW) with size exclusion chromatography (SEC), for fragmentation by capillary electrophoresis (CE-SDS), and for chemical modification (for example deamidation, isomerization, or oxidation) by LC-MS peptide mapping. After 4 weeks at 35° C., CB3f exhibits Δ % HMW of 0.5%, Δ % fragments of 0.6%, and no CDR chemical modifications greater than 0.2%.

Freeze/thaw stability under the same conditions is evaluated using a 3 repeated slow, controlled temperature cycle which mimics the freeze/thaw conditions of large volumes of bulk drug substance placed at −70° C. CB3f exhibits Δ % HMW of 1.9% as measured by SEC after the 3 freeze-thaw cycles. Other excipients can further reduce % HMW growth (data unshown).

These results indicate CB3f possesses good physical and chemical stabilities.

Solubility

Solubility is assessed by concentrating 100 mg of CB3f with a 30 kDa molecular weight cut-off centrifugal filter (for example, Amicon U.C. filters, Millipore, catalog #UFC903024) to a volume of approximately 0.5 mL. The final concentration of the sample is measured by UV absorbance at 280 nm using a Solo VPE spectrophotometer (C Technologies, Inc).

CB3f displays a solubility of greater than or equal to 183 mg/mL in 5 mM histidine pH 6 buffer and greater than or equal to 170 mg/mL in PBS (phosphate-buffered saline) pH 7.4. These results indicate that CB3f exhibits high solubility.

Viscosity

Viscosity of CB3f is analyzed at 15° C. at an approximate concentration of 125 mg/mL in 5 mM histidine at pH 6.0 with different excipients. Viscosity measurements are made with a VROC Initium (RheoSense). CB3f exhibited viscosities of 14.2 cP at 131 mg/mL in 5 mM histidine at pH 6+280 mM mannitol, 9.5 cP in 5 mM histidine at pH 6.0+150 mM sodium chloride, and 6.1 cP viscosity in 5 mM histidine pH 6.0+280 mM arginine. These results indicate that CB3f exhibits low viscosity, which could enable high concentration dosing.

Pharmacokinetics (PK)

PK properties of CB3f is studied in cynomolgus monkeys following a single subcutaneous administration of 0.03, 0.3, 1 and 10 mg/kg of CB3f, or a single intravenous bolus administration of 1 mg/kg of CB3f. CB3f shows linear PK over the subcutaneous dose range examined, with the terminal half-life ($T_{1/2}$) ranging from 182 to 301 hours. The $T_{1/2}$ after a single intravenous bolus administration of 1 mg/kg of CB3f is 324 hours.

It has been reported that obexelimab has an average $T_{1/2}$ of 3.5±1.0 days, which equal to 60-108 hours (Jaraczewska-Baumann, et al., European League Against Rheumatism (EULAR) 2015 Annual Meeting Poster: *A Phase 1b/2a Study of the Safety, Tolerability, Pharmacokinetics and Pharmacodynamics of XmAb®5871 in Patients with Rheumatoid Arthritis*, Jun. 12, 2015, available at https://investors.xencor.com/static-files/0017dcf1-deb2-46eb-93ff-90ba164ec50c). Therefore, CB3f has a better $T_{1/2}$ than obexelimab.

Example 3. In Vitro Functional Characterization of the Anti-Human CD19 Antibodies In Vitro Inhibition of B Cell Proliferation by the Anti-Human CD19 mAb CB3f.

The ability of the anti-human CD19 mAb CB3f to inhibit proliferation of primary human B cells is tested in an in vitro B cell proliferation assay.

Primary human B cells are isolated from healthy donor PBMCs by negative selection using a B cell isolation kit (Stemcell Technologies). Human primary B cells are re-suspended at $1 \times 10^6$ cells/mL and cultured at 37° C. in polystyrene 96-well, u-bottom plates in complete medium (RPMI-1640 containing 10% Fetal bovine serum, 1×MEM-nonessential amino acids, 1 mM Sodium Pyruvate, 1× Penicillin-Streptomycin Solution (all from Corning) and 1× Glutamax (Gibco), 0.1% β-mercaptoethanol (Life Technologies). Cells are pre-treated with anti-human CD19 antibody for 1 hour and stimulated with mouse anti-human IgM (2 µg/mL-Southern Biotech) plus rabbit anti-mouse IgG (12 µg/mL-Thermo Fisher) for 2 days at 37° and 5% CO$_2$. Cells are then pulsed with [$^3$H]-thymidine (1 µCi thymidine/well, PerkinElmer, Boston, Mass.) for 18 hours of cell culture. The level of incorporation of [$^3$H]-thymidine is measured by 2450 Microplate Counter (MicroBeta$^2$ serial number: 5129186, PerkinElmer, Boston, Mass.) and expressed as a cell count per minute (c.c.p.m).

Figure 3:
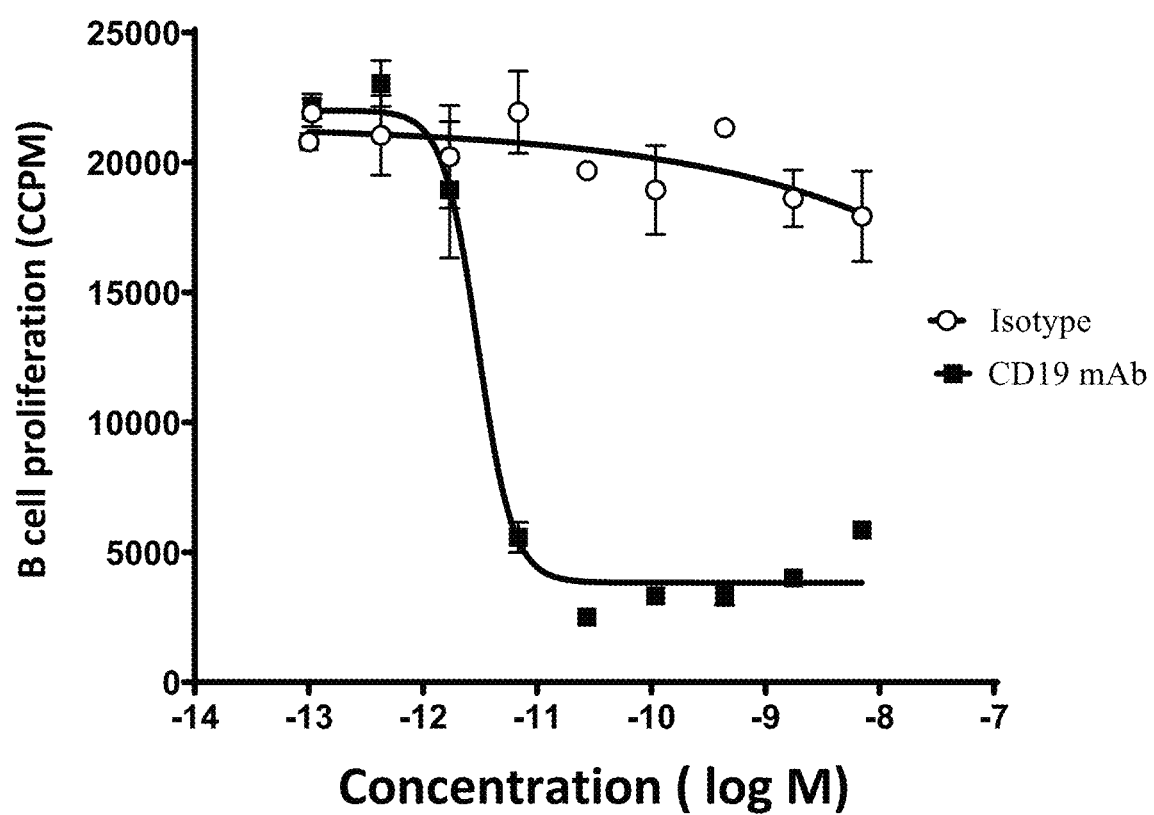
FIG. 3 shows the inhibition of primary B cell proliferation by the anti-human CD19 mAb CB3f.

The anti-human CD19 mAb CB3f inhibits the proliferation of primary human B cells in a dose dependent manner, while the isotype control does not demonstrate inhibition at any tested concentration (FIG. 3). The inhibitory function of CB3f is tested using B cells obtained from 12 different donors, and the average IC$_{50}$ for CB3f is 0.007 nM (Table 3). The data show that the anti-human CD19 mAb CB3f can inhibit proliferation of primary human B cells in a dose dependent manner, while B cell proliferation is not affected by the isotype control antibody.

TABLE 3

Inhibition of primary B cell proliferation by the anti-human CD19 mAb CB3f

| | IC$_{50}$ Values (nM) |
|---|---|
| Donor 1 | 0.006 |
| Donor 2 | 0.009 |
| Donor 3 | 0.003 |
| Donor 4 | 0.006 |
| Donor 5 | 0.004 |
| Donor 6 | 0.003 |
| Donor 7 | 0.003 |
| Donor 8 | 0.005 |
| Donor 9 | 0.005 |
| Donor 10 | 0.028 |
| Donor 11 | 0.004 |
| Donor 12 | 0.005 |
| Average | 0.007 |

In Vitro Inhibition of B Cell Activation in Human Whole Blood

The ability of the anti-human CD19 mAb CB3f to inhibit activation of primary human B cells in whole blood is tested in an in vitro whole blood activation assay.

EDTA treated human whole blood (Healthy donors, TSRI Normal Blood Donor Services, San Diego, Calif.) is cultured in polystyrene 96-well, u-bottom plates and pre-incubated with CB3f or the isotype control antibody for 30 minutes to one hour at 37° C. and 5% CO$_2$. 7 nM of each antibody is used as the highest concentration with 4 fold dilution and 12 points titration in complete medium (RPMI-1640 containing 10% fetal bovine serum, 1×MEM-nonessential amino acids, 1 mM sodium pyruvate, 1× penicillin-streptomycin Solution (all from Corning) and 1× Glutamax (Gibco), 0.1% β-mercaptoethanol (Life Technologies). Whole blood is stimulated with 2.5 µg/mL of TLR9 ligand for 24 hours at 37° C. and 5% CO$_2$ (CpG ODN 7909 (InvivoGen, San Diego, Calif.)). B cell activation profile is measured by flow cytometry and data is analyzed using FlowJo software.

Flow cytometry is performed as follows. Treated and activated human whole blood is lysed with RBC lysis buffer (Fisherscientific, USA). Cells are stained with the appropriate combination of fluorochrome-conjugated antibodies for 30 min at 4° C. to identify B cell activation markers: CD69 BV605 (cat #310938) from BioLegend. Cells are also stained with CD3 FITC (cat #300306), CD19 APC (cat #363006) all from BioLegend, CD20 PerCP-Cy5.5 (cat #560736) from BD Pharminogen and fixable viability dye eFluor™ 780 (eBioscience). At least 25,000-50,000 events gated on living cells are analyzed for each sample. Samples are acquired on a BD Fortessa X-20 and results are analyzed using FlowJo Software.

Figure 4:
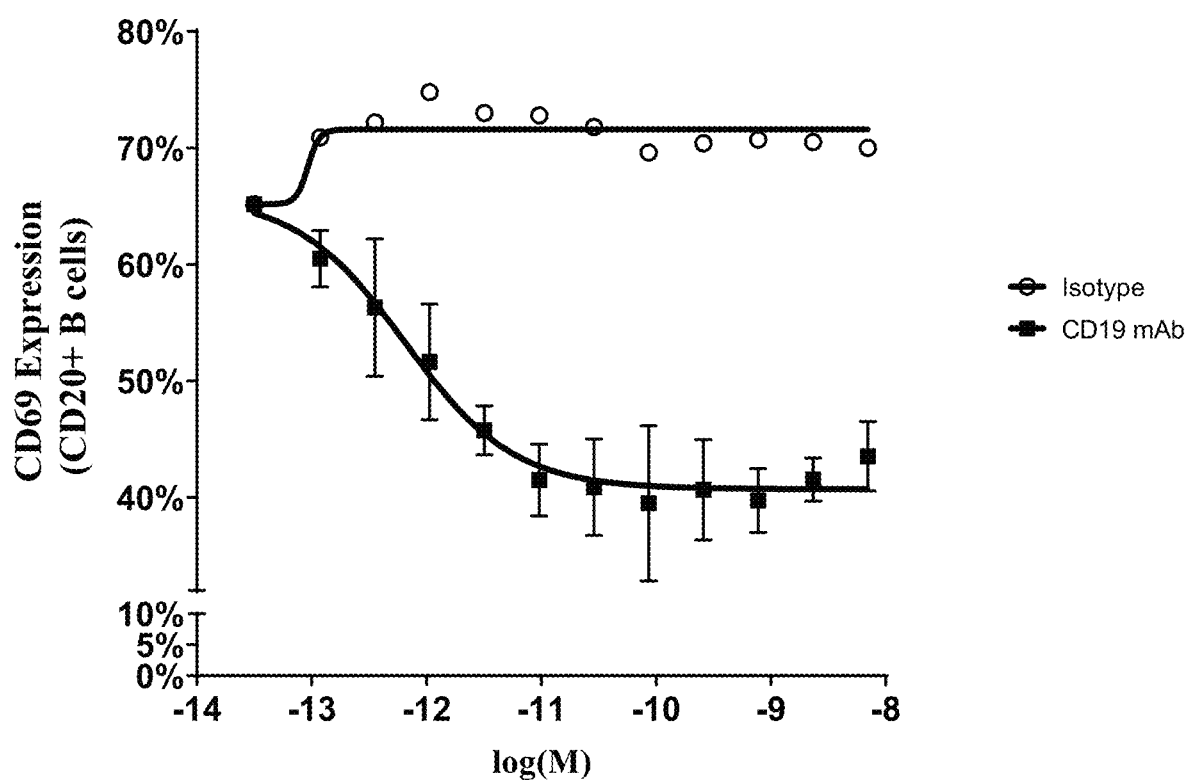
FIG. 4 shows the inhibition of B cell activation in whole blood by the anti-human CD19 mAb CB3f.

The anti-human CD19 mAb CB3f inhibits activation of primary human B cells in a dose dependent manner, which is measured by the reduction of CD69+ B cells. The assay is performed using blood obtained from three different donors and representative results are shown in FIG. 4. The average IC$_{50}$ for CB3f in this assay is 0.008 nM (Table 4). The isotype control antibody did not demonstrate inhibition of CD69 expression at any tested concentration. The data show that anti-human CD19 mAb CB3f can inhibit activation of primary human B cells in whole blood in a dose dependent manner, while B cell activation is not affected by the isotype control antibody.

TABLE 4

Inhibition of B cell activation in whole blood by anti-human CD19 mAb CB3f

| | IC$_{50}$ Values (nM) |
|---|---|
| Donor 1 | 0.015 |
| Donor 2 | 0.0006 |
| Donor 3 | 0.008 |
| Average | 0.008 |

In Vitro Inhibition of B Cell Differentiation into Plasmablasts

Memory human B cells are isolated from healthy donor PBMCs using a Memory B cell Isolation Kit (Miltenyi Biotec). Human primary memory B cells are re-suspended at $1\times10^6$ cells/mL and cultured at 37° C. in polystyrene 96-well, u-bottom plates in complete medium (RPMI-1640 containing 10% fetal bovine serum, 1×MEM-nonessential amino acids, 1 mM sodium pyruvate, 1× penicillin-streptomycin solution (all from Corning) and 1× Glutamax (Gibco), 0.1% β-mercaptoethanol (Life Technologies). Cells are pre-treated with anti-human CD19 mAb CB3f for 1 hour and stimulated with 50 ng/mL anti-CD40, 200 ng/mL BAFF, 1 ng/mL IL-2, 100 ng/mL IL-21 (all from R&D) for 5 days. Cells are washed and stained with the appropriate combination of fluorochrome-conjugated antibodies for 30 min at 4° C. to identify differentiation of memory B cells into plasmablasts: CD38 PE, CD3 FITC (cat #300306), CD19 APC (cat #363006) all from BioLegend, CD20 PerCP-Cy5.5 (cat. #560736) from BD Pharminogen and fixable viability dye eFluor™ 780, eBioscience. At least 25,000-50,000 events gated on living cells are analyzed for each sample. Samples are acquired on a BD Fortessa X-20 and results are analyzed using FLowJo Software. Percent of plasmablasts is defined as % of CD38$^{bright}$/CD20$^{low}$ B cells.

Figure 5:
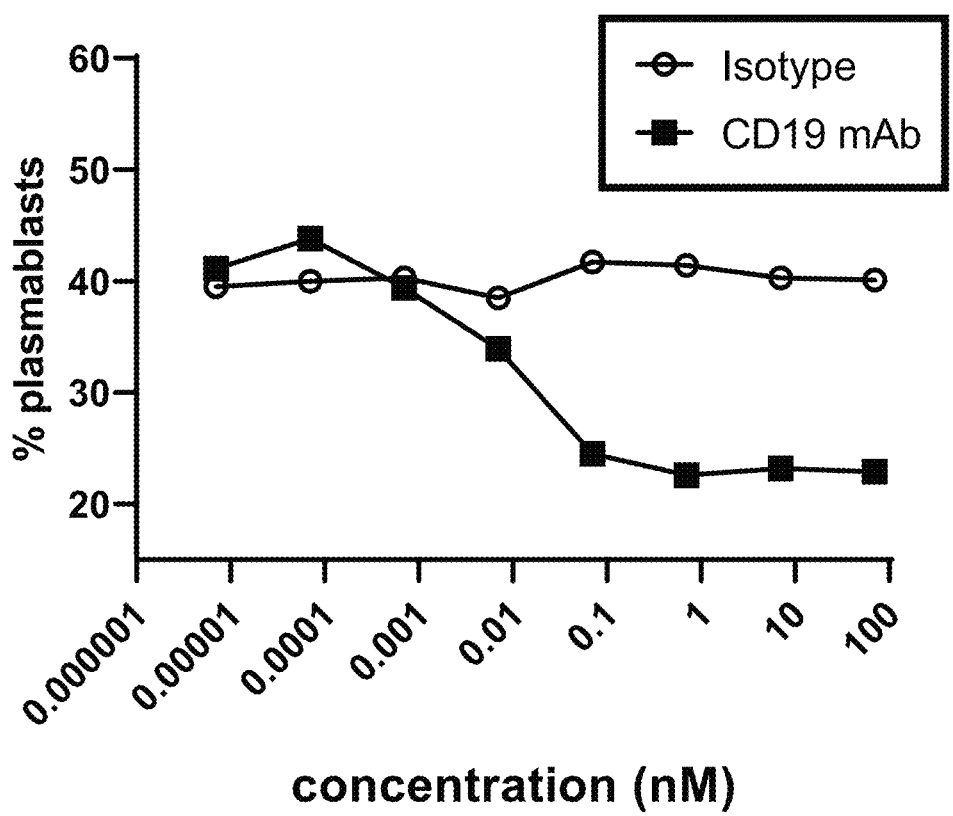
FIG. 5 shows the inhibition of B cell differentiation into plasmablasts by the anti-human CD19 mAb CB3f.

The anti-human CD19 mAb CB3f inhibits differentiation of primary human memory B cells into plasmablasts in a dose dependent manner (FIG. 5). The experiment is repeated three times and the representative data is shown. The isotype control antibody does not demonstrate inhibition of plasmablast differentiation at any tested concentration. The data show that the CB3f can inhibit differentiation of primary human memory B cells into plasmablasts in a dose dependent manner, while the differentiation is not affected by the isotype control antibody.

CD19 mAb CB3f is a Non-Depleting mAb and Lacks Activity in In Vitro CDC and ADCC Assays.

The anti-human CD19 mAb CB3f is a B cell inhibitory antibody, which is designed to inhibit B cell function without causing B cell depletion. In vitro assays are performed to confirm CB3f lacks Complement-Dependent Cytotoxicity (CDC) and Antibody-Dependent Cellular Cytotoxicity (ADCC) activities, which imply that it does not have depleting function.

Wil2-s cell line expressing CD19 and CD20 are used as target cells, and Jurkat cell lines expressing functional FcγRIIIa (V158)-NFAT-Luc (Eli Lilly and Company) are used as the effector cell line. CB3f is tested and an IgG1 antibody that is a known potent inducer of ADCC and CDC is used as a positive control.

CB3f is serially-diluted in triplicates starting at 10 µg/mL and 1 µg/mL test concentrations for the CDC and ADCC assay, respectively. 50 µL/well test compound or assay buffer are added to 96-well plate (Costar 3916). Wil2-s cells are diluted to a concentration of $1\times10^6$ cells/mL and added 50 µL/well to plate. CDC and ADCC plates are incubated for 1 hour at 37° C. Next, Jurkat V158 cells are diluted to a concentration of $3\times10^6$ cells/mL and added 50 µL/well for ADCC plate, or 50 µL/well of pre-diluted complement from human serum (Quidel A113) for CDC plate. CDC plates are incubated at 37° C. for 2 hours followed by addition of 100 µL/well Cell-Titre Glo (Promega G7571). The ADCC plates are incubated at 37° C. for 4 hours followed by addition of 100 µL/well ONE-Glo (Promega E8130). The contents of the plates are mixed using a plate shaker at low speed, and luminescence signal is read on an Envision 11 multi-mode plate reader using 0.2 cps integration. Data is analyzed using GraphPad Prism v8.2.

Figure 6A:
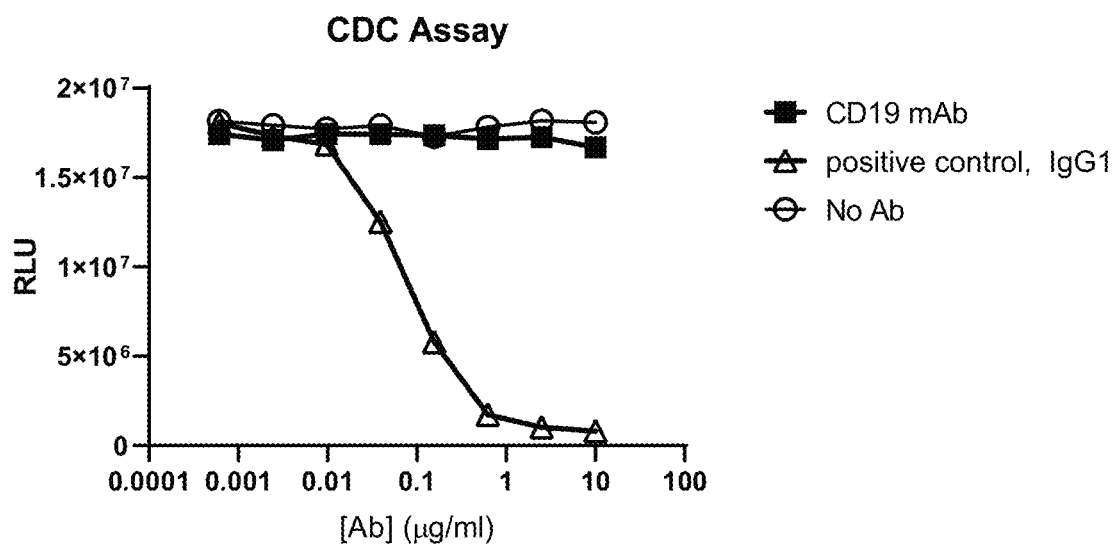
FIGS. 6A-6B show the anti-human CD19 mAb CB3f lacks CDC (FIG. 6A) and ADCC (FIG. 6B) activities.
Figure 6B:
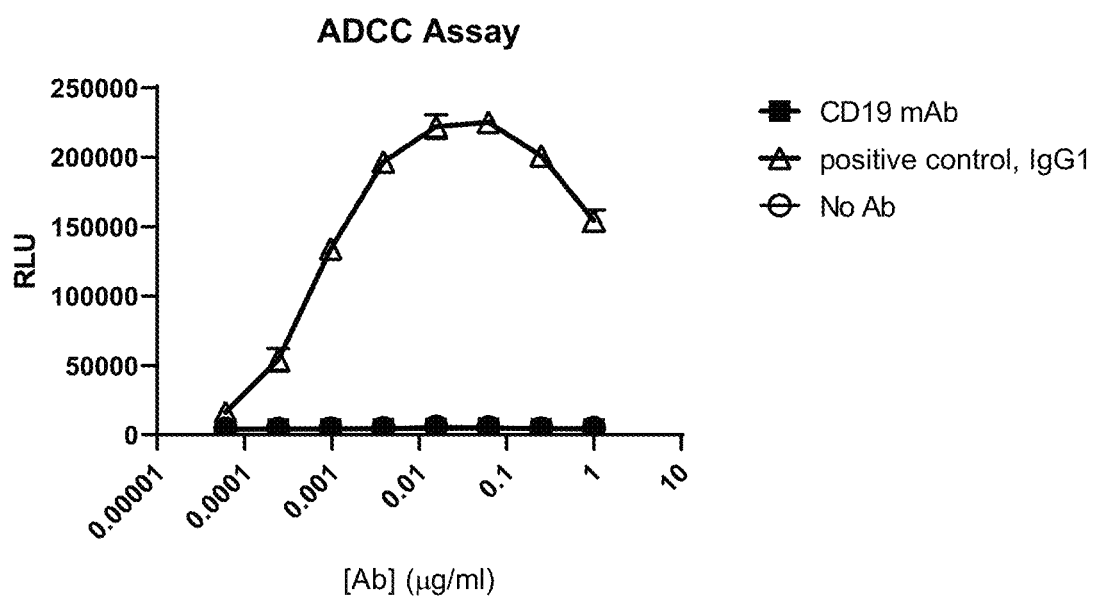

The results of the CDC and ADCC assays are shown in FIGS. 6A-6B (representative results from three independent plate runs). All response levels are classified relative to the positive control IgG1 antibody. The anti-human CD19 mAb CB3f has no CDC activity (FIG. 6A) nor ADCC activity (FIG. 6B) at the indicated concentrations.

Specificity of Anti-Human CD19 mAb Binding to B Cells in Human Whole Blood.

The anti-human CD19 mAb CB3f is a B cell inhibitory antibody, which acts by suppressing B cell function. Obexelimab is an antibody that binds both CD19 and FcγRIIb. However, high affinity binding of obexelimab to FcγRIIb could lead to binding to other cell types in a CD19-independent manner. Therefore, the binding specificity of obexelimab and anti-human CD19 mAb CB3f is compared using a human whole blood binding assay.

EDTA treated human whole blood (Healthy donors, TSRI Normal Blood Donor Services, San Diego, Calif.) is plated in polystyrene 96-well and stained with different concentration of Alexa Flour® 647 conjugated CB3f, Alexa Flour® 647 conjugated and Alexa Flour® 647 conjugated isotype control plus appropriate combination of fluorochrome-conjugated extracellular antibodies to detect lymphocyte/granulocyte population. 7 nM of each antibody is used as the highest concentration with 3-fold dilution and 8 points titration in DPBS 1× no $Ca^{2+}$, no $Mg^{2+}$ (Dulbecco's Phosphate-Buffered Saline) supplemented with 2% of Fetal Bovine Serum (FBS-heat inactivated) both from Corning®. The cocktail includes CD20 PerCP-Cy5.5 (cat #560736), CD45 BV421 (cat #563879), CD66 FITC (cat #555724) all from BD Biosciences. CD3 BV605 (cat #317322), CD11b PE-Cy7 (cat #101216) all from BioLegend and fixable viability dye eFluor™ 780, (cat #65-0865-14) from eBioscience. Whole blood plus antibodies are stained for 30 min at 4° C. in the dark. Dead cells are excluded by viability dye and at least 25,000-50,000 events gated on living cells are analyzed. Samples are acquired on BD Fortessa X-20 and results are analyzed using FlowJo Software.

Figure 7:
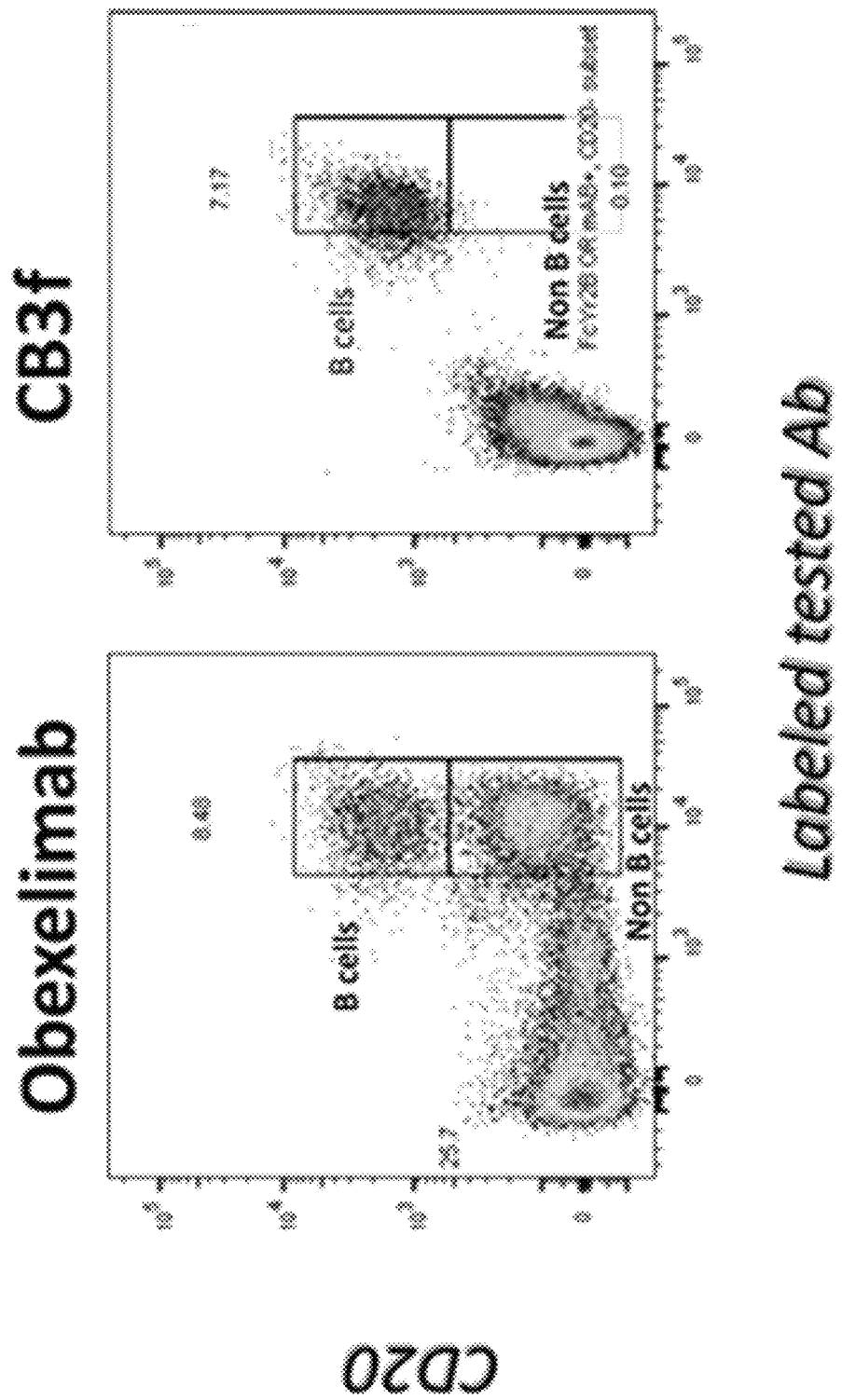
FIG. 7 shows binding specificity of anti-human CD19 mAb CB3f and obexelimab to cells in human whole blood.

Flow cytometry analysis demonstrates that CB3f binds exclusively to B cells in human whole blood at all tested concentrations (FIG. 7). Obexelimab shows binding to human B cells as well as a population of CD20-negative cells (i.e., non-B cells), which express CD66 and CD11b and thus are identified as neutrophils (FIG. 7). Therefore, the data indicate the anti-human CD19 mAb CB3f has highly specific binding to human B cells in human whole blood, whereas obexelimab shows non-specific binding to human neutrophils in addition to B cell binding. Since neutrophil is the most abundant type of white blood cells in human, the nonspecific binding to neutrophils might explain the short half-life of obexelimab observed in human patients. The experiment is repeated using blood from four different donors, representative results are shown in FIG. 7.

In Vitro Apoptosis Assay.

As described above, obexilimab was shown to reduce B cell counts in human patients during clinical studies (Jaraczewska-Baumann, et al., EULAR 2015 Annual Meeting Poster: *A Phase 1b/2a Study of the Safety, Tolerability, Pharmacokinetics and Pharmacodynamics of XmAb®5871 in Patients with Rheumatoid Arthritis*, Jun. 12, 2015).

The ability of the anti-human CD19 mAb CB3f and obexilimab to induce apoptosis of primary human B cells is tested using an in vitro B cell apoptosis assay. Human primary B cells are isolated from healthy donor PBMCs by negative selection using B cell isolation kit (Stemcell Technologies). Human primary B cells are re-suspended at $1\times10^6$ cells/mL and cultured at 37° C. in polystyrene 96-well, u-bottom plates in complete medium (RPMI-1640 containing 10% Fetal bovine serum, 1×MEM-nonessential amino acids, 1 mM sodium pyruvate, 1× penicillin-streptomycin solution (all from Corning) and 1× Glutamax (Gibco), 0.1% β-mercaptoethanol (Life Technologies). Cell are treated with indicated concentrations of CB3f, obexilimab, or an isotype control antibody for 24 hours at 37° C. and 5% $CO_2$. B cell apoptosis is measured by flow cytometry using Annexin V staining in combination with viability dye. Cells are stained with the appropriate combination of fluorochrome-conjugated antibodies for 30 min at 4° C. to identify B cell activation markers: CD19 APC (Biolegend), CD20 PerCP-Cy5.5 (BD Pharminogen), Annexin V (Invitrogen) and fixable viability dye eFluor™ 780 (eBioscience). Apoptotic cells are defined as live Annexin $V^+$ cells. Samples are acquired on a BD Fortessa X-20 and results are analyzed using FlowJo Software.

Figure 8:
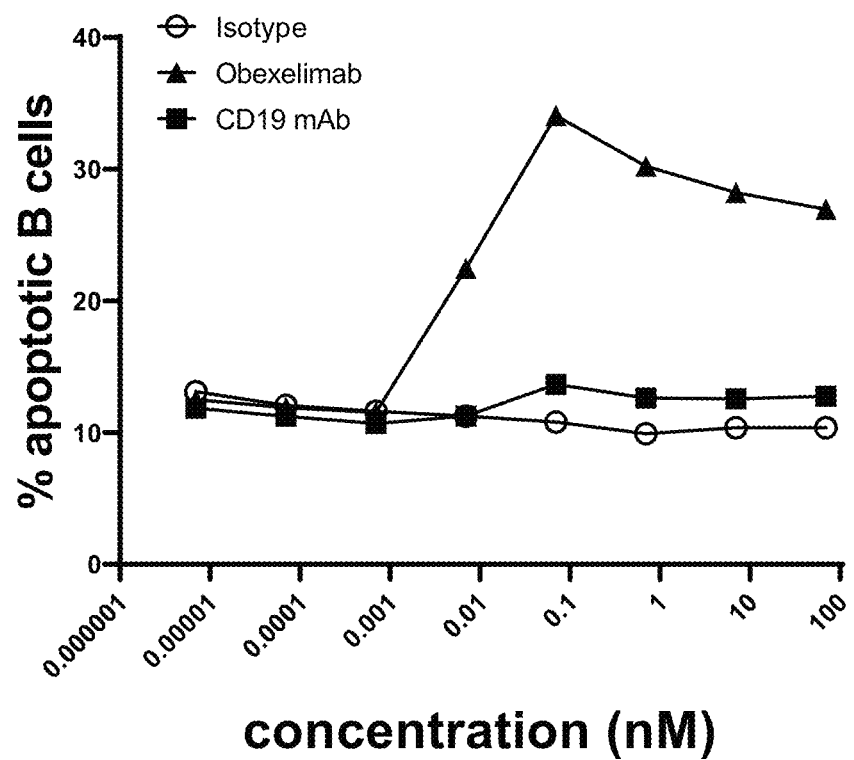
FIG. 8 shows difference in the induction of B cell apoptosis by obexilimab and anti-human CD19 mAb CB3f.

The experiment is repeated using B cells obtained from three different donors and representative data is shown in FIG. 8. Obexilimab induces B cell apoptosis in a dose-dependent manner (FIG. 8), which may explain the reduction of B cell counts in human patients observed in the clinical studies. In contrast, CB3f induces very little to no apoptosis of human B cells when compared to the isotype control (FIG. 8). The data indicates that, in contrast to obexilimab, the anti-human CD19 mAb CB3f does not induce apoptosis of primary human B cells ex vivo, suggesting a different mechanism of action for CB3f. This data further indicates that the anti-human CD19 mAb CB3f acts by inhibiting B cell function without depleting B cells or significantly reducing B cell numbers.

Example 4. In Vivo Functional Characterization of the Anti-Human CD19 Antibodies Female NSG mice (NOD.Cg-Prkdcscid Il2rgtm1Wjl/SzJ, JAX Labs, Stock #05557) are housed 3 per cage at 72° C. under a 12 hour light:dark cycle and allowed food and water ad libitum (n=33). Human peripheral blood mononuclear cells (PBMCs) are isolated from LRS tubes obtained the San Diego Blood Bank (San Diego Calif.) using SepMate 50 Ficol preparation tubes according to the manufacturer's instructions (StemCell Technologies, Vancouver, BC). Freshly isolated PBMCs are suspended in PBS at 1.2 e$^8$ cells/mL and mice are engrafted with 100 μL PBMCs suspension intravenously on day 0 (1.2e$^7$/mouse, n=29); 4 mice are not administered PBMCs as non-engrafted controls. On Day 1, mice are divided into 3 weight matched groups and dosed with human IgG4 isotype control or CB3f at 0.01 or 1.0 mg/kg subcutaneously (200 μL/mouse, n=10, 10, and 9 respectively). Dosing continues once weekly for the remainder of the experiment. Health checks and body weight measurements are performed routinely. Blood is collected by tail snip into heparin coated capillary tubes on Days 6 and 10. On Day 15, blood is collected by cardiac puncture under isoflurane anesthesia into EDTA tubes for FACS analysis and clarified by centrifugation for plasma analyses. Spleens are harvested and processed to single cell suspensions for FACS analyses.

Mice are weighed in a BSL2 hood and assessed for clinical signs of distress 2-3 times/week. Clinical signs common to this model are scruffy hair, hunched body, wasting, and labored breathing or movement. Body weight change is calculated as a percentage of their baseline weight: (Day (x) weight/Day 0 weight)*100.

Blood from the cardiac puncture is collected into EDTA coated tubes, clarified by centrifugation, and the resultant plasma is stored at −80° C. for future processing. Plasma IgM levels are measured using the Mesoscale Discovery Human Isotyping panel (Rockville Md.) according to the manufacturer's instructions.

Single cell suspensions of mouse spleens are used for FACS analysis. Cells are plated in 96-well plates and stained with the appropriate combination of fluorochrome-conjugated antibodies for 30 min at 4° C. to identify B cell activation markers: hCD45-BV421, CD86 BV650, CD3 APC, CD19 FTIC all from BioLegend, CD20 PerCP-Cy5.5 and fixable viability dye eFluor™ 780. At least 250,000 events gated on living cells are analyzed for each sample. Samples are acquired on a BD Fortessa X-20 and results are analyzed using FlowJo Software. Data is graphed and statistics are calculated using Prism Software (GraphPad, San Diego, Calif.). Differences in weights between groups are determined by 2-way RM-ANOVA with Tukey's post hoc test. Differences in plasma IgM levels are determined by 1-way ANOVA with Tukey's post hoc test and considered significant if p<0.05.

Figure 9A:
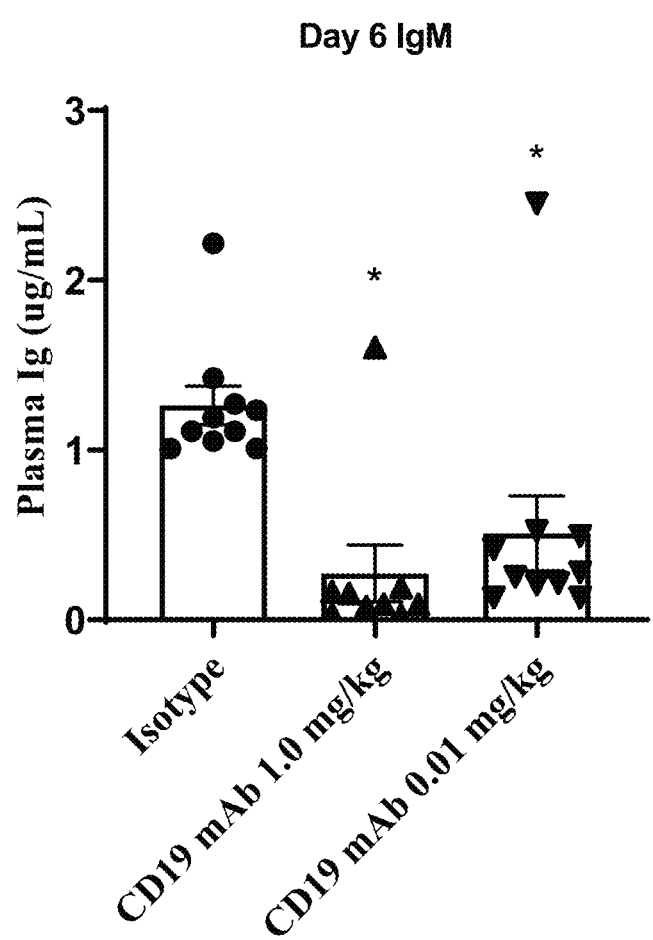

Injection of human PBMCs into NSG mice results in marked engraftment of functional B cells as measured by secretion of human IgM into the periphery. Human IgM in the IgG4 isotype control treated animals increases rapidly from non-detectable to 1.3±0.1 and 48.8±6.2 μg/mL at Days 6 and 10 post engraftments, respectively. CB3f dosed at 0.01 and 1.0 mg/kg/wk significantly attenuates the secretion of IgM by 60% and 78% on Day 6 as shown in FIGS. 9A-9B (p<0.01 for both doses). A 57% reduction in circulating IgM is also observed on Day 10 with the 1.0 mg/kg/wk dose of CB3f (p<0.05). Mouse weights are not different between groups, nor does any mouse display signs of GvHD.

Figure 10:
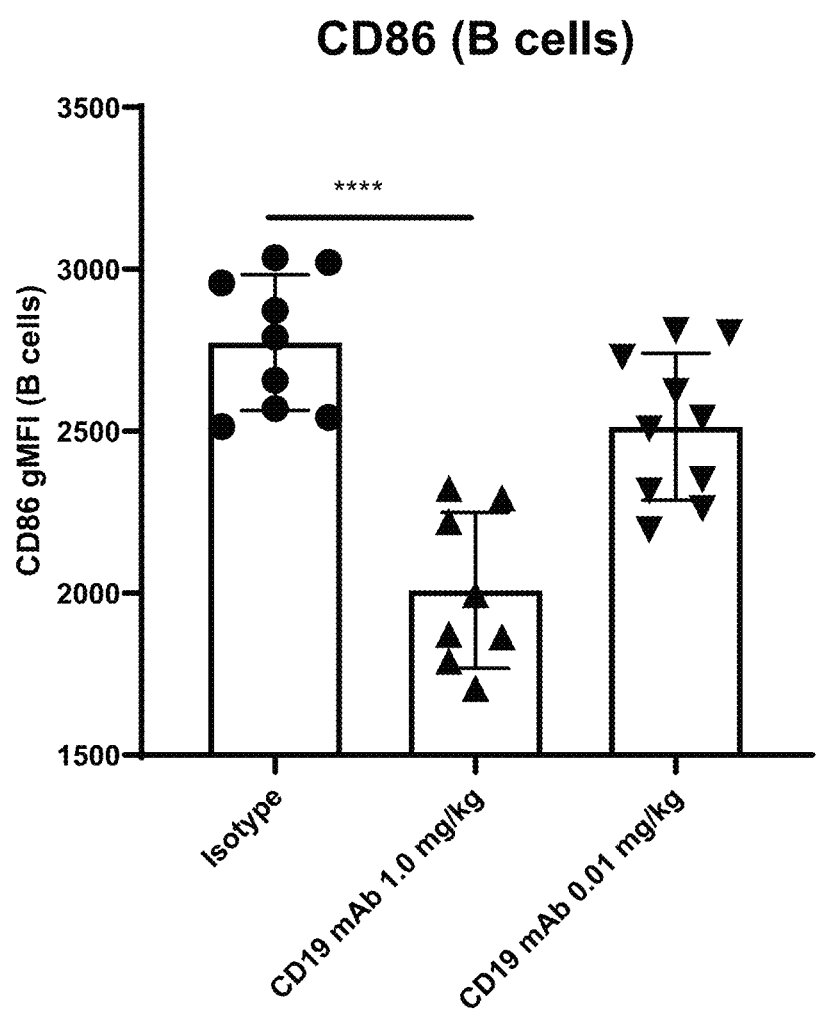
FIG. 10 shows the reduction of CD86 expression on human B cells in NSG mice treated with anti-human CD19 mAb CB3f.

Activation of human B cells in NSG mice is measured by the expression of activation marker CD86. As demonstrated in FIG. 10, treatment with anti-human CD19 mAb CB3f reduces the expression of CD86 on human B cells in a dose-dependent manner.

Figure 11:
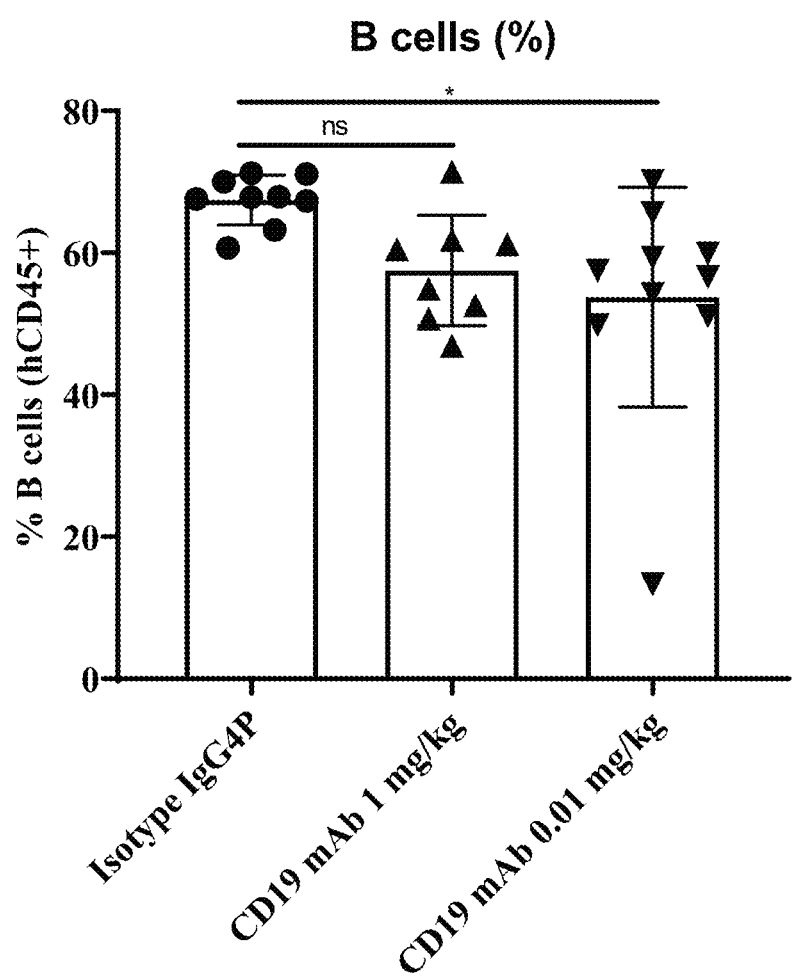
FIG. 11 shows the frequency of B cells in NSG mice treated with anti-human CD19 mAb CB3f.

Treatment with CB3f causes mild reduction in the percentage of splenic B cells, which is probably due to reduced B cell activation and proliferation. Despite this fact, B cells are present in spleens in mostly unaltered numbers (>50% of splenocytes), indicating non-depleting nature of the anti-human CD19 mAb CB3f (FIG. 11).

Example 5. Internalization of the Anti-Human CD19 Antibodies in Primary Human B Cells Peripheral blood mononuclear cells (PBMCs) are collected from LRS-WBC of healthy volunteers using standard density gradient centrifugation method. Human primary B cells are isolated from healthy donor PBMCs by negative selection using B cell isolation kit. For the internalization study, B cells are resuspended at 4×10$^6$ cells/mL and 50 μL is added to each well in a 96 well plate. A labeled F(ab')2 targeting human Ig Fcγ fragment (F(ab')2-TAMRA-QSY7) is used as a probe to track internalization. The test antibody is incubated with probe at 4° C. for 30 minutes to form complex and 50 μL is added to the B cells in each well. The final concentration of the test antibody is 2 μg/mL. Cells are incubated for 24 h at 37° C. in a $CO_2$ incubator. Cells are then washed twice with 2% FBS PBS and resuspeneded in 2% FBS PBS with a viability dye (SYTOX Green, Invitrogen). Data is collected on a BD Fortessa X-20 and analyzed in FlowJo.

Figure 12:
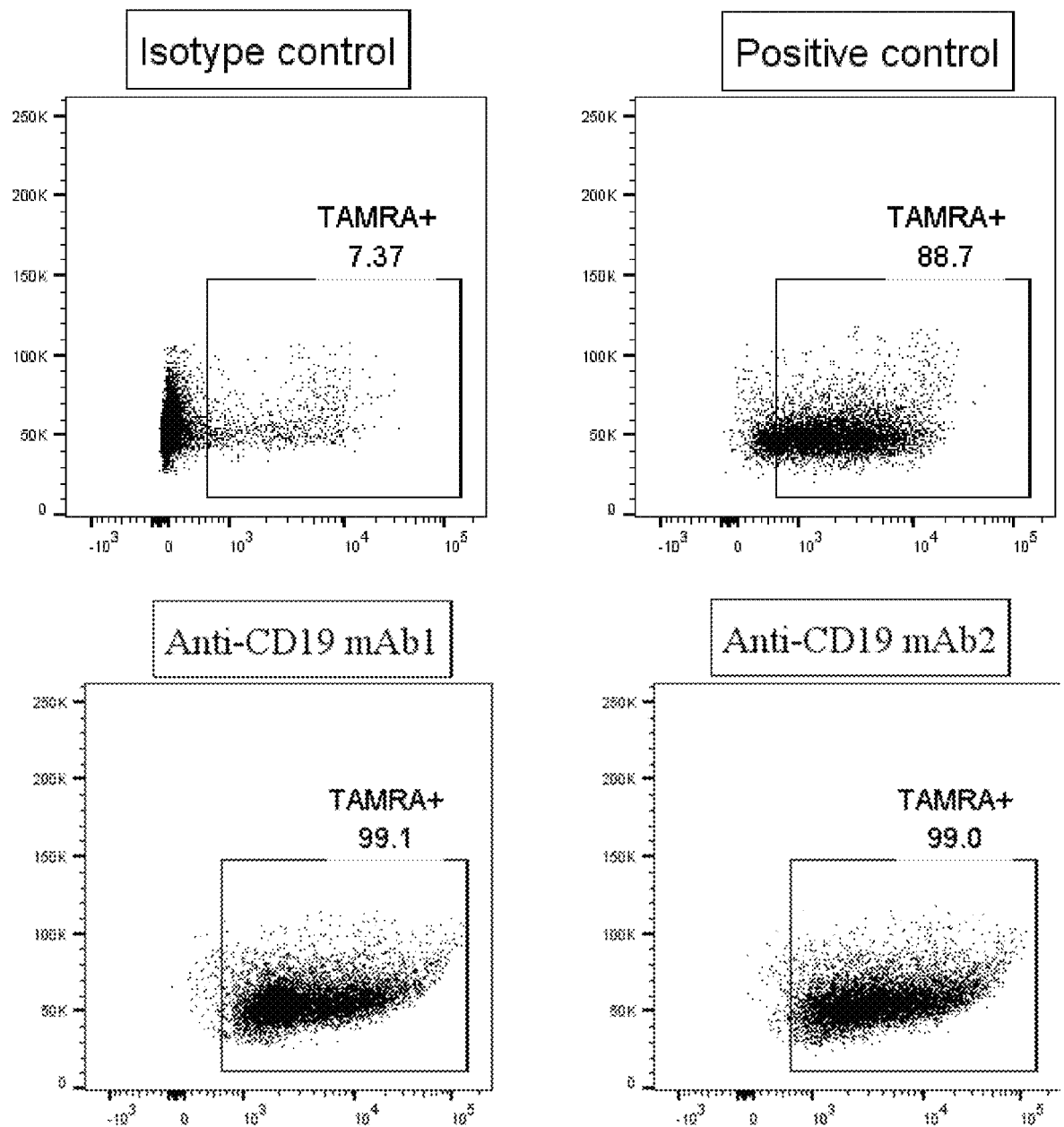
FIG. 12 shows the internalization of anti-human CD19 mAb1 (CB3f) and anti-human CD19 mAb2 (C323.C1) in primary human B cells.

Both anti-human CD19 mAb1 (CB3f) and anti-human CD19 mAb2 (C323.C1) demonstrate internalization in primary human B cells at 24 hours (FIG. 12). An IgG1 effector null isotype control antibody is used as a negative control and does not show any significant internalization as demonstrated by low percentage of TAMRA+ cells (FIG. 12). A positive control IgG4 mAb demonstrates internalization comparable to the tested anti-human CD19 mAbs (FIG. 12).

Example 6. Comparison of the Efficacy of a Non-Depleting Anti-Mouse CD19 Surrogate Antibody with a B Cell Depleting Anti-Mouse CD20 Surrogate Antibody in Animal Models In Vivo Efficacy of a Non-Depleting CD19 Surrogate Antibody and a B Cell Depleting CD20 Surrogate Antibody in a Mouse CIA Model In this study, a non-depleting anti-mouse CD19 surrogate antibody (CD19 surrogate Ab) and a B cell depleting anti-mouse CD20 surrogate antibody (CD20 surrogate Ab) were tested along with an isotype control antibody in a mouse collagen-induced arthritis (CIA) model in a semi-established disease mode (i.e., the antibody was introduced after the induction of the disease but before animals developed any detectable clinical score).

Figure 13A:
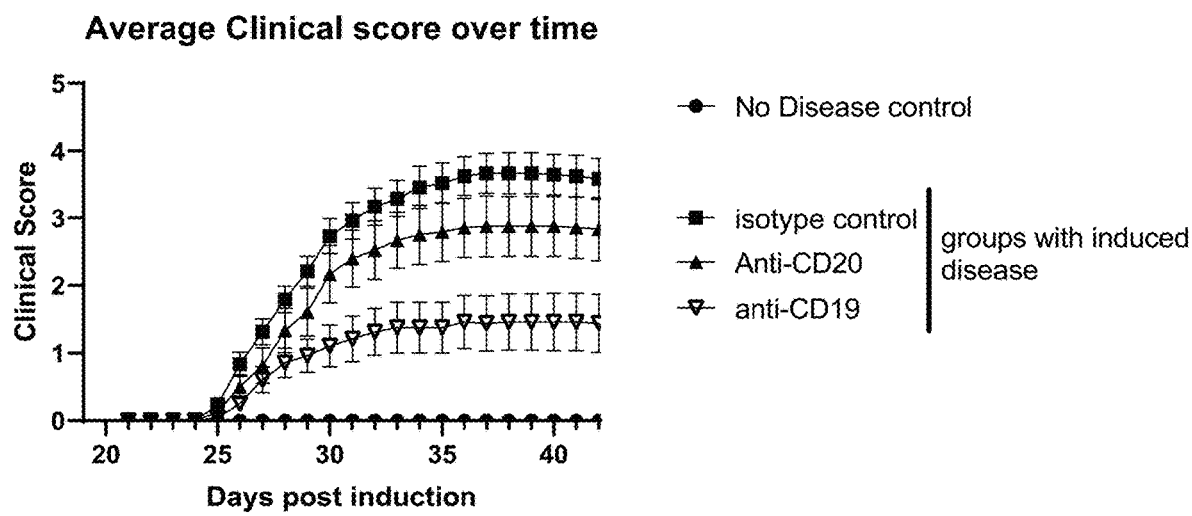
FIGS. 13A-13B show comparison of the efficacy of a non-depleting CD19 surrogate Ab and a depleting CD20 surrogate Ab in the mouse collagen-induced arthritis (CIA) model.
Figure 13B:
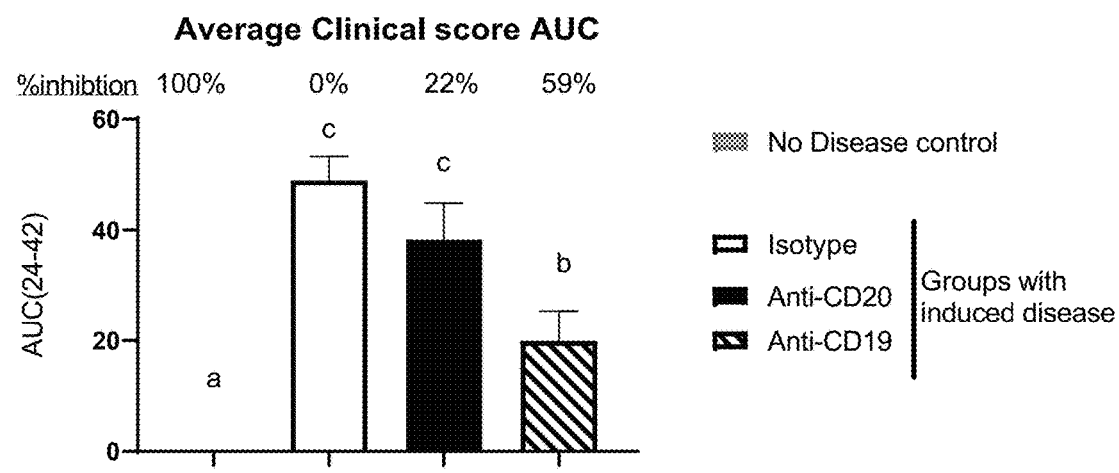

Isotype control treated mice immunized with collagen and complete Freund's adjuvant (CFA) developed observable signs of joint inflammation starting on Day 25, while isotype treated non-diseased mice had no observable joint inflammation throughout the study (FIG. 13A). Treatment starting on Day 19 with the CD20 surrogate Ab (10 mg/kg SC, once weekly) ameliorated average clinical score, whereas the CD19 surrogate Ab (5 mg/kg SC, twice weekly) reduced average clinical scores even more (FIG. 13A). The CD20 surrogate Ab did not significantly reduce clinical score AUC compared to isotype control (FIG. 13B). On the other hand, the CD19 surrogate Ab significantly reduced clinical score AUC compared to both isotype control and the CD20 surrogate Ab (FIG. 13B). These results suggest that the CD19 surrogate Ab can reduce disease severity greater than the CD20 surrogate Ab as assessed by clinical score AUC in the CIA model of mouse arthritis conducted in semi-established mode.

In Vivo Efficacy of the Non-Depleting CD19 Surrogate Ab and the B Cell Depleting CD20 Surrogate Ab in a Mouse NOD Model of Type 1 Diabetes.

The NOD/ShiLtJ mouse strain (commonly called Non-Obese Diabetic) is a polygenic model for autoimmune type 1 diabetes (T1D). Diabetes in NOD mice is characterized by hyperglycemia and insulitis, a leukocytic infiltration of the pancreatic islets. Prevalence of disease is highest in female mice.

In this study, the non-depleting CD19 surrogate Ab was tested along with a depleting CD20 surrogate Ab in the mouse NOD model of Type 1 diabetes in a semi-therapeutic disease mode (i.e., the antibody was introduced just before the control animals started to develop clinical score).

Figure 14:
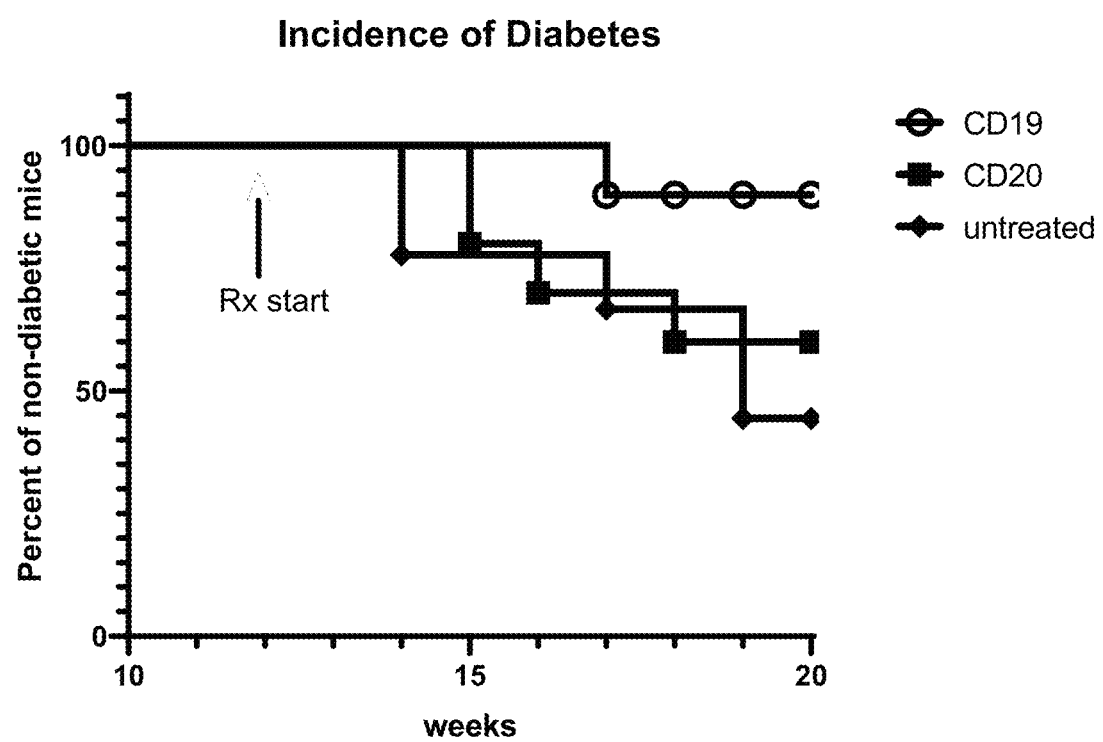
FIG. 14 shows treatment with the non-depleting CD19 surrogate Ab in semi-therapeutic mode delayed and reduced incidence of diabetes greater than the depleting CD20 surrogate Ab in the NOD model of Type 1 diabetes. Incidence of diabetes (mice with blood glucose levels above 240 mg/dl were considered as diabetic>. n=10/group except n=9 for untreated group). Animals were dosed starting at 12 weeks of age.

Female NOD-LTJ mice were left untreated, dosed with 5 mg/kg/BIW of the CD19 surrogate Ab, or the CD20 surrogate Ab starting at 12 weeks of age. All mice were tested weekly for blood glucose using an Accu Check Aviva blood glucose meter (Roche cat #06870287001) and test strips (Roche cat #06908373001 lot #497064). Mice with blood glucose levels above 240 mg/dl were considered as diabetic. Untreated mice developed diabetes starting of 14 weeks of age. Treatment with the CD20 surrogate Ab (5 mg/kg SC, twice weekly) demonstrated very mild protection from the disease progression, whereas the CD19 surrogate Ab (5 mg/kg SC, twice weekly) delayed and reduced the incidence of diabetes (FIG. 14). These results suggest that the non-depleting CD19 surrogate Ab can delay and reduce the incidence of type 1 diabetes in NOD mice greater than the depleting anti-CD20 surrogate Ab.

In Vivo Efficacy of the Non-Depleting CD19 Surrogate Ab and the B Cell Depleting CD20 Surrogate Ab in a Mouse EAE Model Mouse experimental autoimmune encephalomyelitis (EAE) has been widely used as model of inflammatory neurodegenerative and demyelinating diseases, such as multiple sclerosis (MS).

In this study, the non-depleting anti-CD19 surrogate Ab was tested along with the depleting CD20 surrogate Ab in proteolipid protein (PLP) induced remitting-relapsing (RR) demyelinating EAE model in a semi-therapeutic disease mode (i.e., the antibody was introduced after the induction of the disease, but before animals started developing any detectable clinical score).

Figure 15:
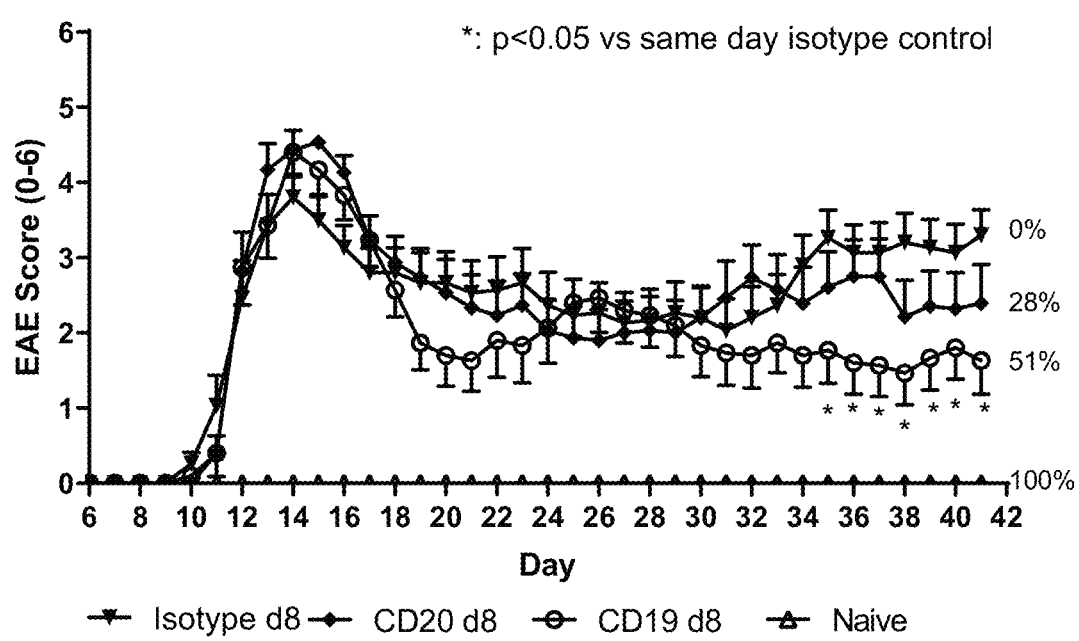
FIG. 15 shows treatment with the non-depleting CD19 surrogate Ab in semi-therapeutic mode reduced clinical score greater than the depleting CD20 surrogate Ab in the mouse EAE model. Clinical scores of mice between Day 6 and Day 42 of the study (n=12/group). Symbols represent mean of group and error bars represent standard error of the mean (SEM). Animals were dosed starting Day 6. * $p<0.05$ vs same day isotype control.

Female 9-10 weeks old SJL mice (Jackson Labs), with a mean body weight of 18-21 g were used for the study. Mice were immunized with Hooke Kit™ PLP139-151/CFA Emulsion (catalog number EK-0120, Hooke Laboratories, Lawrence Mass.), and 75 ng pertussis toxin (PTX). Animals were randomized based on body weight into study groups with 15 mice in each group. The non-depleting CD19 surrogate Ab, the depleting CD20 surrogate Ab or isotype mouse IgG1 control of 5 mg/kg was given subcutaneously twice a week starting on day 8. EAE score was collected daily with scale 0-6 in 0.5 unit increments. Mice were sacrificed on day 42. Treatment with the non-depleting CD19 surrogate Ab significantly reduces EAE score on day 35-41 compared to isotype control; with a 51% decrease in EAE score on the final day (FIG. 15). Treatment with the depleting CD20 surrogate Ab did not demonstrate significant reduction of disease score over isotype control at any tested time points (FIG. 15). These results suggest that the non-depleting CD19 surrogate Ab can reduce disease severity greater than the depleting CD20 surrogate Ab as assessed by clinical score in the EAE model of multiple sclerosis in semi-therapeutic mode of treatment.

The invention claimed is:

1. An antibody that binds human CD19, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein
the HCDR1 comprises SEQ ID NO: 29,
the HCDR2 comprises SEQ ID NO: 30,
the HCDR3 comprises SEQ ID NO: 31,
the LCDR1 comprises SEQ ID NO: 32,
the LCDR2 comprises SEQ ID NO: 33, and
the LCDR3 comprises SEQ ID NO: 34.

2. The antibody of claim 1, wherein the VH comprises SEQ ID NO: 37 and the VL comprises SEQ ID NO: 41.

3. The antibody of claim 1, wherein the antibody comprises a heavy chain (HC) comprising SEQ ID NO: 35 and a light chain (LC) comprising SEQ ID NO: 39.

4. The antibody of claim 1, wherein the antibody comprises a HC comprising SEQ ID NO: 52 and a LC comprising SEQ ID NO: 39.

5. An antibody that binds human CD19, wherein the antibody comprises a VH and a VL, wherein the VH comprises HCDR1, HCDR2, and HCDR3, and the VL comprises LCDR1, LCDR2, and LCDR3, wherein
the HCDR1 comprises SEQ ID NO: 29,
the HCDR2 comprises SEQ ID NO: 30,
the HCDR3 comprises SEQ ID NO: 31,
the LCDR1 comprises SEQ ID NO: 43,
the LCDR2 comprises SEQ ID NO: 44, and
the LCDR3 comprises SEQ ID NO: 45.

6. The antibody of claim 5, wherein the VH comprises SEQ ID NO: 37 and the VL comprises SEQ ID NO: 48.

7. The antibody of claim 5, wherein the antibody comprises a HC comprising SEQ ID NO: 35 and a LC comprising SEQ ID NO: 46.

8. The antibody of claim 5, wherein the antibody comprises a HC comprising SEQ ID NO: 52 and a LC comprising SEQ ID NO: 46.

9. An antibody that binds human CD19, wherein the antibody comprises a VH and a VL, wherein the VH comprises HCDR1, HCDR2, and HCDR3, and the VL comprises LCDR1, LCDR2, and LCDR3, wherein the HCDR1 comprises SEQ ID NO: 15,
the HCDR2 comprises SEQ ID NO: 16,
the HCDR3 comprises SEQ ID NO: 17,
the LCDR1 comprises SEQ ID NO: 18,
the LCDR2 comprises SEQ ID NO: 19, and
the LCDR3 comprises SEQ ID NO: 20.

10. The antibody of claim 9, wherein the VH comprises SEQ ID NO: 23 and the VL comprises SEQ ID NO: 27.

11. The antibody of claim 9, wherein the antibody comprises a HC comprising SEQ ID NO: 21 and a LC comprising SEQ ID NO: 25.

12. The antibody of claim 9, wherein the antibody comprises a HC comprising SEQ ID NO: 54 and a LC comprising SEQ ID NO: 25.

13. The antibody of claim 1, wherein the antibody is a non-depleting antibody.

14. The antibody of claim 5, wherein the antibody is a non-depleting antibody.

15. The antibody of claim 9, wherein the antibody is a non-depleting antibody.

16. A nucleic acid comprising a sequence encoding SEQ ID NO: 35, 52, 39, 46, 21, 54, or 25.

17. A vector comprising the nucleic acid of claim 16.

18. The vector of claim 17, wherein the vector comprises a first nucleic acid sequence encoding SEQ ID NO: 35 or 52, and a second nucleic acid sequence encoding SEQ ID NO: 39 or 46.

19. The vector of claim 17, wherein the vector comprises a first nucleic acid sequence encoding SEQ ID NO: 21 or 54, and a second nucleic acid sequence encoding SEQ ID NO: 25.

20. A composition comprising a first vector comprising a nucleic acid sequence encoding SEQ ID NO: 35 or 52, and a second vector comprising a nucleic acid sequence encoding SEQ ID NO: 39 or 46.

21. A composition comprising a first vector comprising a nucleic acid sequence encoding SEQ ID NO: 21 or 54, and a second vector comprising a nucleic acid sequence encoding SEQ ID NO: 25.

22. A cell comprising the vector of claim 17.

23. A cell comprising the vector of claim 18.

24. A cell comprising the vector of claim 19.

25. A cell comprising a first vector comprising a nucleic acid sequence encoding SEQ ID NO: 35 or 52, and a second vector comprising a nucleic acid sequence encoding SEQ ID NO: 39 or 46.

26. A cell comprising a first vector comprising a nucleic acid sequence encoding SEQ ID NO: 21 or 54, and a second vector comprising a nucleic acid sequence encoding SEQ ID NO: 25.

27. The cell of claim 22, wherein the cell is a mammalian cell.

28. The cell of claim 23, wherein the cell is a mammalian cell.

29. The cell of claim 24, wherein the cell is a mammalian cell.

30. The cell of claim 25, wherein the cell is a mammalian cell.

31. The cell of claim 26, wherein the cell is a mammalian cell.

32. A process of producing an antibody comprising culturing the cell of claim 23 under conditions such that the antibody is expressed and recovering the expressed antibody from the culture medium.

33. A process of producing an antibody comprising culturing the cell of claim 24 under conditions such that the antibody is expressed and recovering the expressed antibody from the culture medium.

34. A process of producing an antibody comprising culturing the cell of claim 25 under conditions such that the antibody is expressed and recovering the expressed antibody from the culture medium.

35. A process of producing an antibody comprising culturing the cell of claim 26 under conditions such that the antibody is expressed and recovering the expressed antibody from the culture medium.

36. An antibody produced by the process of claim 32.

37. An antibody produced by the process of claim 33.

38. An antibody produced by the process of claim 34.

39. An antibody produced by the process of claim 35.

40. A pharmaceutical composition comprising the antibody of claim 1, and a pharmaceutically acceptable excipient, diluent or carrier.

41. A pharmaceutical composition comprising the antibody of claim 5, and a pharmaceutically acceptable excipient, diluent or carrier.

42. A pharmaceutical composition comprising the antibody of claim 9, and a pharmaceutically acceptable excipient, diluent or carrier.

43. A method of treating a B cell associated disorder in a subject in need thereof, comprising administering to the subject a therapeutically effective amount of the antibody of claim 1.

44. The method of claim 43, wherein the B cell associated disorder is an autoimmune disease.

45. The method of claim 43, wherein the B cell associated disorder is selected from systemic lupus erythematosus, multiple sclerosis, rheumatoid arthritis, Sjogren's syndrome, idiopathic thrombocytopenia purpura, Type 1 diabetes, pemphigus vulgaris, meuromyelitis optica, ANCA vasculitis, or myasthenia gravis.

46. A method of treating a B cell associated disorder in a subject in need thereof, comprising administering to the subject a therapeutically effective amount of the antibody of claim 5.

47. The method of claim 46, wherein the B cell associated disorder is an autoimmune disease.

48. The method of claim 46, wherein the B cell associated disorder is selected from systemic lupus erythematosus, multiple sclerosis, rheumatoid arthritis, Sjogren's syndrome, idiopathic thrombocytopenia purpura, Type 1 diabetes, pemphigus vulgaris, meuromyelitis optica, ANCA vasculitis, or myasthenia gravis.

49. A method of treating a B cell associated disorder in a subject in need thereof, comprising administering to the subject a therapeutically effective amount of the antibody of claim 9.

50. The method of claim 49, wherein the B cell associated disorder is an autoimmune disease.

51. The method of claim 49, wherein the B cell associated disorder is selected from systemic lupus erythematosus, multiple sclerosis, rheumatoid arthritis, Sjogren's syndrome, idiopathic thrombocytopenia purpura, Type 1 diabetes, pemphigus vulgaris, meuromyelitis optica, ANCA vasculitis, or myasthenia gravis.

* * * * *

UNITED STATES PATENT AND TRADEMARK OFFICE
CERTIFICATE OF CORRECTION

PATENT NO. : 11,623,956 B2
APPLICATION NO. : 17/181184
DATED : April 11, 2023
INVENTOR(S) : Barrett Allan et al.

Page 1 of 1

It is certified that error appears in the above-identified patent and that said Letters Patent is hereby corrected as shown below:

In the Claims

Claims 45, Line 5, meuromyelitis should be neuromyelitis;
Claims 48, Line 5, meuromyelitis should be neuromyelitis; and
Claims 51, Line 5, meuromyelitis should be neuromyelitis.

Signed and Sealed this
Twenty-seventh Day of June, 2023

Katherine Kelly Vidal
*Director of the United States Patent and Trademark Office*

SEQUENCE LISTING

```
<160> NUMBER OF SEQ ID NOS: 57

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Lys Ala Ser Gly Gly Thr Phe Ser Ser Tyr Ala Ile Ser
1               5                   10

<210> SEQ ID NO 2
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 2

Gly Ile Ile Pro Ile Phe Gly Thr Ala Asn
1               5                   10

<210> SEQ ID NO 3
<211> LENGTH: 13
<212> TYPE: PRT
<213> ORGANISM: ARTIFICIAL SEQUENCE
<220> FEATURE:
<223> OTHER INFORMATION: Synthetic Construct
```

```
<400> SEQUENCE: 3

Ala Arg Glu Asp Phe Gly Tyr Asn Tyr Gly Met Asp Val
1               5                   10

<210> SEQ ID NO 4
<211> LENGTH: 12
<212> TYPE: PRT
<213> ORGANISM: ARTIFICIAL SEQUENCE
<220> FEATURE:
<223> OTHER INFORMATION: Synthetic Construct

<400> SEQUENCE: 4

Arg Ala Ser Gln Gly Val Asn Ser Tyr Tyr Leu Ala
1               5                   10

<210> SEQ ID NO 5
<211> LENGTH: 8
<212> TYPE: PRT
<213> ORGANISM: ARTIFICIAL SEQUENCE
<220> FEATURE:
<223> OTHER INFORMATION: Synthetic Construct

<400> SEQUENCE: 5

Tyr Ala Thr Ser Thr Arg Ala Thr
1               5

<210> SEQ ID NO 6
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 6

Gln His Tyr Gly Asn Ser Leu Phe Thr
1               5

<210> SEQ ID NO 7
<211> LENGTH: 446
<212> TYPE: PRT
<213> ORGANISM: ARTIFICIAL SEQUENCE
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Gly Tyr Asn Tyr Gly Met Asp Val Trp Gly Gln
            100                 105                 110

Gly Thr Thr Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 8
<211> LENGTH: 1338
<212> TYPE: DNA
<213> ORGANISM: ARTIFICIAL SEQUENCE
<220> FEATURE:
<223> OTHER INFORMATION: Synthetic Construct

<400> SEQUENCE: 8

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagagaggac   300
```

```
ttcggctaca attacggcat ggacgtctgg ggccaaggga ccacggtcac cgtctcctca    360
gcttctacca agggcccatc ggtcttcccg ctagcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accctgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga gatgaccaag   1080
aaccaggtca gcctgacctg cctggtcaaa ggcttctacc ccagcgacat cgccgtggag   1140
tgggaaagca atgggcagcc ggagaacaac tacaagacca cgcctcccgt gctggactcc   1200
gacggctcct tcttcctcta cagcaggcta accgtggaca agagcaggtg gcaggagggg   1260
aatgtcttct catgctccgt gatgcatgag gctctgcaca accactacac acagaagagc   1320
ctctccctgt ctctgggt                                                 1338
```

<210> SEQ ID NO 9
<211> LENGTH: 120
<212> TYPE: PRT
<213> ORGANISM: ARTIFICIAL SEQUENCE
<220> FEATURE:
<223> OTHER INFORMATION: Synthetic Construct

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Gly Tyr Asn Tyr Gly Met Asp Val Trp Gly Gln
            100                 105                 110

Gly Thr Thr Val Thr Val Ser Ser
        115                 120
```

<210> SEQ ID NO 10
<211> LENGTH: 360
<212> TYPE: DNA
<213> ORGANISM: ARTIFICIAL SEQUENCE
<220> FEATURE:
<223> OTHER INFORMATION: Synthetic Construct

<400> SEQUENCE: 10

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac      180
gcacagaagt tccagggcag agtcacgatt accgcggacg aatccacgag cacagcctac     240
atggagctga gcagcctgag atctgaggac acggccgtgt attactgtgc gagagaggac     300
ttcggctaca attcggcat ggacgtctgg ggccaaggga ccacggtcac cgtctcctca      360
```

<210> SEQ ID NO 11
<211> LENGTH: 215
<212> TYPE: PRT
<213> ORGANISM: ARTIFICIAL SEQUENCE
<220> FEATURE:
<223> OTHER INFORMATION: Synthetic Construct

<400> SEQUENCE: 11

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Gly Val Asn Ser Tyr
             20                  25                  30

Tyr Leu Ala Trp Tyr Gln Gln Lys Pro Gly Gln Ala Pro Arg Leu Leu
         35                  40                  45

Met Tyr Ala Thr Ser Thr Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Asn Ser Leu
                 85                  90                  95

Phe Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 12
<211> LENGTH: 645
<212> TYPE: DNA
<213> ORGANISM: ARTIFICIAL SEQUENCE
<220> FEATURE:
<223> OTHER INFORMATION: Synthetic Construct

<400> SEQUENCE: 12

```
gaaattgtgt tgacacagtc tccaggcacc ctgtctttgt ctccagggga agagccacc      60 ctctcctgca gggccagtca gggtgttaac agctactact tagcctggta ccagcagaaa    120
```

```
cctggccagg ctcccaggct cctcatgtat gctacatcca ccagggccac tggcatccca      180
gacaggttca gtggcagtgg gtctgggaca gacttcactc tcaccatcag cagactggag      240
cctgaagatt ttgcagtgta ttactgtcag cactatggta actcactatt cactttcggc      300
cctgggacca aggtggagat caaacggacc gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgc                     645
```

<210> SEQ ID NO 13
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Val Asn Ser Tyr
            20                  25                  30

Tyr Leu Ala Trp Tyr Gln Gln Lys Pro Gly Gln Ala Pro Arg Leu Leu
        35                  40                  45

Met Tyr Ala Thr Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Asn Ser Leu
                85                  90                  95

Phe Thr Phe Gly Pro Gly Thr Lys Val Glu Ile Lys
            100                 105
```

<210> SEQ ID NO 14
<211> LENGTH: 324
<212> TYPE: DNA
<213> ORGANISM: ARTIFICIAL SEQUENCE
<220> FEATURE:
<223> OTHER INFORMATION: Synthetic Construct

<400> SEQUENCE: 14

```
gaaattgtgt tgacacagtc tccaggcacc ctgtctttgt ctccagggga aagagccacc       60
ctctcctgca gggccagtca gggtgttaac agctactact tagcctggta ccagcagaaa      120
cctggccagg ctcccaggct cctcatgtat gctacatcca ccagggccac tggcatccca      180
gacaggttca gtggcagtgg gtctgggaca gacttcactc tcaccatcag cagactggag      240
cctgaagatt ttgcagtgta ttactgtcag cactatggta actcactatt cactttcggc      300
cctgggacca aggtggagat caaa                                             324
```

<210> SEQ ID NO 15
<211> LENGTH: 13
<212> TYPE: PRT
<213> ORGANISM: ARTIFICIAL SEQUENCE
<220> FEATURE:
<223> OTHER INFORMATION: Synthetic Construct

```
<400> SEQUENCE: 15

Lys Ala Ser Gly Gly Thr Ile Ser Ser Tyr Ala Tyr Ser
1               5                   10

<210> SEQ ID NO 16
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 16

Gly Ile Ile Pro Ile Phe Asp Thr Ala Asn
1               5                   10

<210> SEQ ID NO 17
<211> LENGTH: 13
<212> TYPE: PRT
<213> ORGANISM: ARTIFICIAL SEQUENCE
<220> FEATURE:
<223> OTHER INFORMATION: Synthetic Construct

<400> SEQUENCE: 17

Ala Arg Glu Asp Phe Gly Tyr Asn Tyr Ala Met Asp Val
1               5                   10

<210> SEQ ID NO 18
<211> LENGTH: 12
<212> TYPE: PRT
<213> ORGANISM: ARTIFICIAL SEQUENCE
<220> FEATURE:
<223> OTHER INFORMATION: Synthetic Construct

<400> SEQUENCE: 18

Arg Ala Ser Gln Lys Val Asn Ser Tyr Tyr Leu His
1               5                   10

<210> SEQ ID NO 19
<211> LENGTH: 8
<212> TYPE: PRT
<213> ORGANISM: ARTIFICIAL SEQUENCE
<220> FEATURE:
<223> OTHER INFORMATION: Synthetic Construct

<400> SEQUENCE: 19

Tyr Ala Thr Arg Thr Arg Pro Thr
1               5

<210> SEQ ID NO 20
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 20

Gln His Tyr Gly Gln Ser Leu Phe Thr
1               5

<210> SEQ ID NO 21
<211> LENGTH: 446
<212> TYPE: PRT
<213> ORGANISM: ARTIFICIAL SEQUENCE
<220> FEATURE:
<223> OTHER INFORMATION: Synthetic Construct
```

<400> SEQUENCE: 21

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Ile Ser Ser Tyr
            20                  25                  30
Ala Tyr Ser Trp Val Arg Gln Ala Pro Gly Gln Gly Leu Glu Trp Met
        35                  40                  45
Gly Gly Ile Ile Pro Ile Phe Asp Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Asp Phe Gly Tyr Asn Tyr Ala Met Asp Val Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
        435                 440                 445

<210> SEQ ID NO 22
<211> LENGTH: 1338
<212> TYPE: DNA
<213> ORGANISM: ARTIFICIAL SEQUENCE
<220> FEATURE:
<223> OTHER INFORMATION: Synthetic Construct

<400> SEQUENCE: 22
caggtgcagc tggtgcagtc tggggctgag gtgaagaagc ctgggtcctc ggtgaaggtc      60
tcctgcaagg cttctggagg caccattagc agctatgctt acagctgggt gcgacaggcc     120
cctggacaag gcttgagtg gatgggaggg atcatcccta tctttgacac agcaaactac     180
gcacagaagt tccagggcag agtcacgatt accgcggacg aatccacgag cacagcctac     240
atggagctga gcagcctgag atctgaggac acggccgtgt attactgtgc gagagaggac     300
ttcggctaca attacgcgat ggacgtctgg ggccaaggga cccttgtcac cgtctcctca     360
gcttctacca agggcccatc ggtcttcccg ctagcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accctgccca gcacctgagt tctggggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggaaagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggt                                                  1338

<210> SEQ ID NO 23
<211> LENGTH: 120
<212> TYPE: PRT
<213> ORGANISM: ARTIFICIAL SEQUENCE
<220> FEATURE:
<223> OTHER INFORMATION: Synthetic Construct

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ile Ser Ser Tyr
            20                  25                  30

```
Ala Tyr Ser Trp Val Arg Gln Ala Pro Gly Gln Gly Leu Glu Trp Met
            35                  40                  45
Gly Gly Ile Ile Pro Ile Phe Asp Thr Ala Asn Tyr Ala Gln Lys Phe
 50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Asp Phe Gly Tyr Asn Tyr Ala Met Asp Val Trp Gly Gln
            100                 105                 110
Gly Thr Leu Val Thr Val Ser Ser
            115                 120
```

<210> SEQ ID NO 24
<211> LENGTH: 360
<212> TYPE: DNA
<213> ORGANISM: ARTIFICIAL SEQUENCE
<220> FEATURE:
<223> OTHER INFORMATION: Synthetic Construct

<400> SEQUENCE: 24

```
caggtgcagc tggtgcagtc tggggctgag gtgaagaagc ctgggtcctc ggtgaaggtc    60
tcctgcaagg cttctggagg caccattagc agctatgctt acagctgggt gcgacaggcc   120
cctggacaag gcttgagtg gatgggaggg atcatcccta tctttgacac agcaaactac   180
gcacagaagt tccagggcag agtcacgatt accgcggacg aatccacgag cacagcctac   240
atggagctga gcagcctgag atctgaggac acggccgtgt attactgtgc gagagaggac   300
ttcggctaca attacgcgat ggacgtctgg ggccaaggga cccttgtcac cgtctcctca   360
```

<210> SEQ ID NO 25
<211> LENGTH: 215
<212> TYPE: PRT
<213> ORGANISM: ARTIFICIAL SEQUENCE
<220> FEATURE:
<223> OTHER INFORMATION: Synthetic Construct

<400> SEQUENCE: 25

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Lys Val Asn Ser Tyr
            20                  25                  30
Tyr Leu His Trp Tyr Gln Gln Lys Pro Gly Gln Ala Pro Arg Leu Leu
            35                  40                  45
Ile Tyr Ala Thr Arg Thr Arg Pro Thr Gly Ile Pro Asp Arg Phe Ser
 50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln His Tyr Gly Gln Ser Leu
                85                  90                  95
Phe Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
```

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 26
<211> LENGTH: 645
<212> TYPE: DNA
<213> ORGANISM: ARTIFICIAL SEQUENCE
<220> FEATURE:
<223> OTHER INFORMATION: Synthetic Construct

<400> SEQUENCE: 26
gaaattgtgt tgacacagtc tccaggcacc ctgtctttgt ctccagggga aagagccacc      60
ctctcctgca gggccagtca gaaagttaac agctactact acattggta ccagcagaaa     120 cctggccagg ctcccaggct cctcatctat gctacaagaa ccaggccaac tggcatccca     180
gacaggttca gtggcagtgg gtctgggaca gacttcactc tcaccatcag cagactggag     240
cctgaagatt ttgcagtgta ttactgtcag cactatggtc agtcactatt cactttcggc     300
caggggacca aggtggagat caaacggacc gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag acagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgc                     645

<210> SEQ ID NO 27
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Lys Val Asn Ser Tyr
            20                  25                  30

Tyr Leu His Trp Tyr Gln Gln Lys Pro Gly Gln Ala Pro Arg Leu Leu
        35                  40                  45

Ile Tyr Ala Thr Arg Thr Arg Pro Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Gln Ser Leu
                85                  90                  95

Phe Thr Phe Gly Gln Gly Thr Lys Val Glu Ile Lys
            100                 105

-continued

<210> SEQ ID NO 28
<211> LENGTH: 324
<212> TYPE: DNA
<213> ORGANISM: ARTIFICIAL SEQUENCE
<220> FEATURE:
<223> OTHER INFORMATION: Synthetic Construct

<400> SEQUENCE: 28

```
gaaattgtgt tgacacagtc tccaggcacc ctgtctttgt ctccagggga aagagccacc      60
ctctcctgca gggccagtca gaaagttaac agctactact tacattggta ccagcagaaa     120
cctggccagg ctcccaggct cctcatctat gctacaagaa ccaggccaac tggcatccca     180
gacaggttca gtggcagtgg gtctgggaca gacttcactc tcaccatcag cagactggag     240
cctgaagatt ttgcagtgta ttactgtcag cactatggtc agtcactatt cactttcggc     300
caggggacca aggtggagat caaa                                            324
```

<210> SEQ ID NO 29
<211> LENGTH: 13
<212> TYPE: PRT
<213> ORGANISM: ARTIFICIAL SEQUENCE
<220> FEATURE:
<223> OTHER INFORMATION: Synthetic Construct

<400> SEQUENCE: 29

Lys Ala Ser Gly His Thr Ile Ser Ser Tyr Ala Tyr Ser
1               5                   10

<210> SEQ ID NO 30
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 30

Asp Ile Ile Pro Ala Tyr Gly Ser Pro Asn
1               5                   10

<210> SEQ ID NO 31
<211> LENGTH: 13
<212> TYPE: PRT
<213> ORGANISM: ARTIFICIAL SEQUENCE
<220> FEATURE:
<223> OTHER INFORMATION: Synthetic Construct

<400> SEQUENCE: 31

Ala Arg Glu Asp Phe Gly Lys Asn Tyr Ala Met Asp Val
1               5                   10

<210> SEQ ID NO 32
<211> LENGTH: 12
<212> TYPE: PRT
<213> ORGANISM: ARTIFICIAL SEQUENCE
<220> FEATURE:
<223> OTHER INFORMATION: Synthetic Construct

<400> SEQUENCE: 32

Arg Ala Ser Gln His Val Ser Ser His Tyr Leu Ala
1               5                   10

<210> SEQ ID NO 33
<211> LENGTH: 8
<212> TYPE: PRT
<213> ORGANISM: ARTIFICIAL SEQUENCE

```
<220> FEATURE:
<223> OTHER INFORMATION: Synthetic Construct

<400> SEQUENCE: 33

Tyr Gly Ala Ser Ser Arg Ala Thr
1               5

<210> SEQ ID NO 34
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 34

Gln His Tyr Gly Gln Ser Gln Phe Thr
1               5

<210> SEQ ID NO 35
<211> LENGTH: 446
<212> TYPE: PRT
<213> ORGANISM: ARTIFICIAL SEQUENCE
<220> FEATURE:
<223> OTHER INFORMATION: Synthetic Construct

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly His Thr Ile Ser Ser Tyr
            20                  25                  30

Ala Tyr Ser Trp Val Arg Gln Ala Pro Gly Gln Gly Leu Glu Trp Met
        35                  40                  45

Gly Asp Ile Ile Pro Ala Tyr Gly Ser Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Gly Lys Asn Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 36
<211> LENGTH: 1338
<212> TYPE: DNA
<213> ORGANISM: ARTIFICIAL SEQUENCE
<220> FEATURE:
<223> OTHER INFORMATION: Synthetic Construct

<400> SEQUENCE: 36
caggtgcagc tggtgcagtc tggggctgag gtgaagaagc ctgggtcctc ggtgaaggtc      60
tcctgcaagg cttctggaca taccattagc agctatgctt acagctgggt gcgacaggcc     120
cctggacaag ggcttgagtg gatgggagac atcatccctg cctatggctc accaaactac     180
gcacagaagt tccagggcag agtcacgatt accgcggacg aatccacgag cacagcctac     240
atggagctga gcagcctgag atctgaggac acggccgtgt attactgtgc gagagaggac     300
ttcggcaaga attacgcgat ggacgtctgg ggccaaggga cccttgtcac cgtctcctca     360
gcttctacca agggcccatc ggtcttcccg ctagcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc cccatgccc accctgccca gcacctgagt ttctgggggg accatcagtc     720
ttcctgttcc cccaaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
```

```
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggaaagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggt                                                  1338

<210> SEQ ID NO 37
<211> LENGTH: 120
<212> TYPE: PRT
<213> ORGANISM: ARTIFICIAL SEQUENCE
<220> FEATURE:
<223> OTHER INFORMATION: Synthetic Construct

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly His Thr Ile Ser Ser Tyr
            20                  25                  30

Ala Tyr Ser Trp Val Arg Gln Ala Pro Gly Gln Gly Leu Glu Trp Met
        35                  40                  45

Gly Asp Ile Ile Pro Ala Tyr Gly Ser Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Gly Lys Asn Tyr Ala Met Asp Val Trp Gly Gln
            100                 105                 110

Gly Thr Leu Val Thr Val Ser Ser
        115                 120

<210> SEQ ID NO 38
<211> LENGTH: 360
<212> TYPE: DNA
<213> ORGANISM: ARTIFICIAL SEQUENCE
<220> FEATURE:
<223> OTHER INFORMATION: Synthetic Construct

<400> SEQUENCE: 38
caggtgcagc tggtgcagtc tggggctgag gtgaagaagc ctgggtcctc ggtgaaggtc      60
tcctgcaagg cttctggaca taccattagc agctatgctt acagctgggt gcgacaggcc    120
cctggacaag gcttgagtg gatgggagac atcatccctg cctatggctc accaaactac    180
gcacagaagt tccagggcag agtcacgatt accgcggacg aatccacgag cacagcctac    240
atggagctga gcagcctgag atctgaggac acggccgtgt attactgtgc gagagaggac    300
ttcggcaaga attacgcgat ggacgtctgg ggccaaggga cccttgtcac cgtctcctca    360

<210> SEQ ID NO 39
<211> LENGTH: 215
<212> TYPE: PRT
<213> ORGANISM: ARTIFICIAL SEQUENCE
<220> FEATURE:
<223> OTHER INFORMATION: Synthetic Construct
```

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Ser Ser His
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Gln Ser Gln
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 40
<211> LENGTH: 645
<212> TYPE: DNA
<213> ORGANISM: ARTIFICIAL SEQUENCE
<220> FEATURE:
<223> OTHER INFORMATION: Synthetic Construct

<400> SEQUENCE: 40
gaaattgtgt tgacacagtc tccaggcacc ctgtctttgt ctccagggga aagagccacc      60
ctctcctgca gggccagtca gcatgttagc agccactact tagcttggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cactatggtc agtcacagtt cactttcggc     300
caggggacca aggtggagat caaacggacc gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgc                    645

<210> SEQ ID NO 41
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Ser Ser His
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Gln Ser Gln
                85                  90                  95

Phe Thr Phe Gly Gln Gly Thr Lys Val Glu Ile Lys
            100                 105
```

<210> SEQ ID NO 42
<211> LENGTH: 324
<212> TYPE: DNA
<213> ORGANISM: ARTIFICIAL SEQUENCE
<220> FEATURE:
<223> OTHER INFORMATION: Synthetic Construct

<400> SEQUENCE: 42

```
gaaattgtgt tgacacagtc tccaggcacc ctgtctttgt ctccagggga aagagccacc    60
ctctcctgca gggccagtca gcatgttagc agccactact tagcttggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cactatggtc agtcacagtt cactttcggc   300
caggggacca aggtggagat caaa                                          324
```

<210> SEQ ID NO 43
<211> LENGTH: 12
<212> TYPE: PRT
<213> ORGANISM: ARTIFICIAL SEQUENCE
<220> FEATURE:
<223> OTHER INFORMATION: Synthetic Construct

<400> SEQUENCE: 43

```
Arg Ala Ser Gln His Val Asn Ser His Tyr Leu Ala
1               5                   10
```

<210> SEQ ID NO 44
<211> LENGTH: 8
<212> TYPE: PRT
<213> ORGANISM: ARTIFICIAL SEQUENCE
<220> FEATURE:
<223> OTHER INFORMATION: Synthetic Construct

<400> SEQUENCE: 44

```
Tyr Ala Thr Arg Thr Arg Pro Thr
1               5
```

<210> SEQ ID NO 45
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 45

Gln His Tyr Gly Gln Ser Gln Phe Thr
1               5

<210> SEQ ID NO 46
<211> LENGTH: 215
<212> TYPE: PRT
<213> ORGANISM: ARTIFICIAL SEQUENCE
<220> FEATURE:
<223> OTHER INFORMATION: Synthetic Construct

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Asn Ser His
            20                  25                  30

Tyr Leu Ala Trp Tyr Gln Gln Lys Pro Gly Ala Pro Arg Leu Leu
        35                  40                  45

Ile Tyr Ala Thr Arg Thr Arg Pro Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Gln Ser Gln
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 47
<211> LENGTH: 645
<212> TYPE: DNA
<213> ORGANISM: ARTIFICIAL SEQUENCE
<220> FEATURE:
<223> OTHER INFORMATION: Synthetic Construct

<400> SEQUENCE: 47
gaaattgtgt tgacacagtc tccaggcacc ctgtctttgt ctccagggga aagagccacc      60
ctctcctgca gggccagtca gcatgttaac agccactact agcttggta ccagcagaaa     120 cctggccagg ctcccaggct cctcatctat gctacaagaa ccaggccaac tggcatccca     180

```
gacaggttca gtggcagtgg gtctgggaca gacttcactc tcaccatcag cagactggag    240
cctgaagatt ttgcagtgta ttactgtcag cactatggtc agtcacagtt cactttcggc    300
caggggacca aggtggagat caaacggacc gtggctgcac atctgtcttc atcttcccg     360 ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgc                    645
```

<210> SEQ ID NO 48
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 48

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Asn Ser His
            20                  25                  30

Tyr Leu Ala Trp Tyr Gln Gln Lys Pro Gly Gln Ala Pro Arg Leu Leu
        35                  40                  45

Ile Tyr Ala Thr Arg Thr Arg Pro Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Gln Ser Gln
                85                  90                  95

Phe Thr Phe Gly Gln Gly Thr Lys Val Glu Ile Lys
            100                 105
```

<210> SEQ ID NO 49
<211> LENGTH: 324
<212> TYPE: DNA
<213> ORGANISM: ARTIFICIAL SEQUENCE
<220> FEATURE:
<223> OTHER INFORMATION: Synthetic Construct

<400> SEQUENCE: 49

```
gaaattgtgt tgacacagtc tccaggcacc ctgtctttgt ctccagggga aagagccacc     60
ctctcctgca gggccagtca gcatgttaac agccactact tagcttggta ccagcagaaa    120
cctggccagg ctcccaggct cctcatctat gctacaagaa ccaggccaac tggcatccca    180
gacaggttca gtggcagtgg gtctgggaca gacttcactc tcaccatcag cagactggag    240
cctgaagatt ttgcagtgta ttactgtcag cactatggtc agtcacagtt cactttcggc    300
caggggacca aggtggagat caaa                                            324
```

<210> SEQ ID NO 50
<211> LENGTH: 449
<212> TYPE: PRT
<213> ORGANISM: ARTIFICIAL SEQUENCE
<220> FEATURE:
<223> OTHER INFORMATION: Synthetic Construct

```
<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly His Thr Ile Ser Ser Tyr
            20                  25                  30

Ala Tyr Ser Trp Val Arg Gln Ala Pro Gly Gln Gly Leu Glu Trp Met
        35                  40                  45

Gly Asp Ile Ile Pro Ala Tyr Gly Ser Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Gly Lys Asn Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 51
<211> LENGTH: 1347
<212> TYPE: DNA
<213> ORGANISM: ARTIFICIAL SEQUENCE
<220> FEATURE:
<223> OTHER INFORMATION: Synthetic Construct

<400> SEQUENCE: 51
caggtgcagc tggtgcagtc tggggctgag gtgaagaagc ctgggtcctc ggtgaaggtc        60
tcctgcaagg cttctggaca taccattagc agctatgctt acagctgggt gcgacaggcc       120
cctggacaag gcttgagtg gatgggagac atcatccctg cctatggctc accaaactac        180
gcacagaagt tccagggcag agtcacgatt accgcgacg aatccacgag cacagcctac        240
atggagctga gcagcctgag atctgaggac acggccgtgt attactgtgc gagagaggac       300
ttcggcaaga attacgcgat ggacgtctgg ggccaaggga cccttgtcac cgtctcctca       360
gcttctacca agggcccatc ggtcttcccg ctagcaccct cctccaagag cacctctggg       420
ggcacagcgg ccctgggctg cctggtcaag gactacttcc ccgaaccggt gacggtgtcg       480
tggaactcag gcgccctgac cagcggcgtg cacaccttcc cggctgtcct acagtcctca       540
ggactctact ccctcagcag cgtggtgacc gtgccctcca gcagcttggg cacccagacc       600
tacatctgca acgtgaatca caagcccagc aacaccaagg tggacaagaa agttgagccc       660
aaatcttgtg acaaaactca cacatgccca ccgtgcccag cacctgaact cctggggga       720 ccgtcagtct tcctcttccc cccaaaaccc aaggacaccc tcatgatctc ccggacccct       780
gaggtcacat gcgtggtggt ggacgtgagc cacgaagacc ctgaggtcaa gttcaactgg       840
tacgtggacg gcgtggaggt gcataatgcc aagacaaagc cgcgggagga gcagtacaac       900
agcacgtacc gtgtggtcag cgtcctcacc gtcctgcacc aggactggct gaatggcaag       960
gagtacaagt gcaaggtctc caacaaagcc ctcccagccc ccatcgagaa aaccatctcc      1020
aaagccaaag gcagccccg agaaccacag gtgtacaccc tgcccccatc ccgggacgag      1080
ctgaccaaga accaggtcag cctgacctgc ctggtcaaag gcttctatcc cagcgacatc      1140
gccgtggagt gggagagcaa tgggcagccg gagaacaact acaagaccac gcccccgtg      1200 ctggactccg acggctcctt cttcctctat agcaagctca ccgtggacaa gagcaggtgg      1260
cagcagggga acgtcttctc atgctccgtg atgcatgagg ctctgcacaa ccactacaca      1320
cagaagagcc tctccctgtc tccgggt                                          1347

<210> SEQ ID NO 52
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly His Thr Ile Ser Ser Tyr
            20                  25                  30

-continued

```
Ala Tyr Ser Trp Val Arg Gln Ala Pro Gly Gln Gly Leu Glu Trp Met
         35                  40                  45
Gly Asp Ile Ile Pro Ala Tyr Gly Ser Pro Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Ala Arg Glu Asp Phe Gly Lys Asn Tyr Ala Met Asp Val Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Ser Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
```

Glu Ala Leu His Asn His Tyr Thr Gln Lys Ser Leu Ser Leu Ser Pro
            435                 440                 445

Gly Lys
    450

<210> SEQ ID NO 53
<211> LENGTH: 1350
<212> TYPE: DNA
<213> ORGANISM: ARTIFICIAL SEQUENCE
<220> FEATURE:
<223> OTHER INFORMATION: Synthetic Construct

<400> SEQUENCE: 53
caggtgcaac ttgtccaaag cggagctgag gttaagaaac caggttcatc tgtgaaggtg      60
tcatgtaagg caagcggcca caccatttca tcttacgcat actcctgggt cgacaagct     120 ccaggccagg gattggaatg gatgggagac ataatcccag catacggatc acctaactac     180
gcacagaagt ttcaggggag agtgacaatt acagccgacg agtctactag cactgcttac     240
atggagttgt cttcacttcg gtcagaggat acagcagttt actattgtgc cagggaggat     300
ttcgggaaaa attatgctat ggatgtatgg ggtcagggca ccctggttac tgtatcatct     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaagc cgccggggga     720
ccgtcagtct tcctcttccc cccaaaaccc aaggacaccc tcatgatctc ccggacccct     780
gaggtcacat gcgtggtggt gtccgtgagc cacgaagacc ctgaggtcaa gttcaactgg     840
tatgtggacg gcgtggaggt gcataatgcc aagacaaagc cgcgggagga gcagtacaac     900
agcacgtacc gtgtggtcag cgtcctcacc gtcctgcacc aagactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggaggag    1080
atgaccaaga accaagtcag cctgacctgc ctggtcaaag gcttctatcc agcgacatc    1140 gccgtggagt gggagagcaa tgggcagccg gagaacaact acaagaccac gcctcccgtg    1200
ctggactccg acggctcctt cttcctctat tccaagctca ccgtggacaa gagcaggtgg    1260
cagcagggga acgtcttctc atgctccgtg atgcatgagg ctctgcacaa ccactacacg    1320
cagaagagcc tctccctgtc tccgggcaaa                                    1350

<210> SEQ ID NO 54
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ile Ser Ser Tyr
            20                  25                  30

-continued

Ala Tyr Ser Trp Val Arg Gln Ala Pro Gly Gln Gly Leu Glu Trp Met
            35                  40                  45

Gly Gly Ile Ile Pro Ile Phe Asp Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Asp Phe Gly Tyr Asn Tyr Ala Met Asp Val Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 55
<211> LENGTH: 1350
<212> TYPE: DNA
<213> ORGANISM: ARTIFICIAL SEQUENCE
<220> FEATURE:
<223> OTHER INFORMATION: Synthetic Construct

<400> SEQUENCE: 55
caggttcagc tcgtgcaaag tggagctgag gtgaaaaaac ctggttctag cgtcaaggtc      60
tcttgtaagg cctctggggg cactataagc tcttatgctt atagttgggt gcgccaggcc     120
ccaggacagg gcttggaatg gatgggcggc ataataccca tattcgacac agccaactac     180
gctcaaaaat ttcaggggag agtgactata actgcagacg agagcactag caccgcttac     240
atggagttga gtagtctccg cagtgaagac acagccgtct attattgcgc tagggaggac     300
tttggttaca actacgccat ggatgtctgg ggccagggta ctttggtcac cgtatctagt     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaagc cgccggggga     720
ccgtcagtct tcctcttccc cccaaaaccc aaggacaccc tcatgatctc ccggacccct     780
gaggtcacat gcgtggtggt gtccgtgagc cacgaagacc ctgaggtcaa gttcaactgg     840
tatgtggacg gcgtggaggt gcataatgcc aagacaaagc cgcgggagga gcagtacaac     900
agcacgtacc gtgtggtcag cgtcctcacc gtcctgcacc aagactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaagtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat tccaagctca ccgtggacaa gagcaggtgg    1260
cagcagggga acgtcttctc atgctccgtg atgcatgagg ctctgcacaa ccactacacg    1320
cagaagagcc tctccctgtc tccgggcaaa                                     1350

<210> SEQ ID NO 56
<211> LENGTH: 557
<212> TYPE: PRT
<213> ORGANISM: Homo sapiens

<400> SEQUENCE: 56

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

-continued

```
Gln Leu Thr Trp Ser Arg Glu Ser Pro Leu Lys Pro Phe Leu Lys Leu
 50                  55                  60

Ser Leu Gly Leu Pro Gly Leu Gly Ile His Met Arg Pro Leu Ala Ile
 65                  70                  75                  80

Trp Leu Phe Ile Phe Asn Val Ser Gln Gln Met Gly Gly Phe Tyr Leu
                 85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460
```

-continued

```
Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
            485                 490                 495

Gly Ser Gln Ser Tyr Glu Asp Met Arg Gly Ile Leu Tyr Ala Ala Pro
        500                 505                 510

Gln Leu Arg Ser Ile Arg Gly Gln Pro Gly Pro Asn His Glu Glu Asp
    515                 520                 525

Ala Asp Ser Tyr Glu Asn Met Asp Asn Pro Asp Gly Pro Asp Pro Ala
530                 535                 540

Trp Gly Gly Gly Arg Met Gly Thr Trp Ser Thr Arg
545                 550                 555

<210> SEQ ID NO 57
<211> LENGTH: 556
<212> TYPE: PRT
<213> ORGANISM: Homo sapiens

<400> SEQUENCE: 57

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285
```

-continued

```
Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
                355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
                435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
                515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555
```